(12) United States Patent
Valencia et al.

(10) Patent No.: US 7,537,608 B2
(45) Date of Patent: May 26, 2009

(54) STENT WITH VARIABLE CRIMPING DIAMETER

(75) Inventors: Hans Valencia, Berkeley, CA (US); Daniel Gregorich, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 583 days.

(21) Appl. No.: 11/438,934

(22) Filed: May 23, 2006

(65) Prior Publication Data

US 2007/0276464 A1 Nov. 29, 2007

(51) Int. Cl.
A61F 2/06 (2006.01)
(52) U.S. Cl. ..................... 623/1.16; 606/108
(58) Field of Classification Search .......... 623/1.16–1.2
See application file for complete search history.

(56) References Cited

U.S. PATENT DOCUMENTS

| | | | |
|---|---|---|---|
| 5,718,724 A | 2/1998 | Goicoechea et al. | 623/1 |
| 5,749,825 A | 5/1998 | Fischell et al. | 600/3 |
| 5,938,697 A | 8/1999 | Killion et al. | 623/1 |
| 6,017,363 A | 1/2000 | Hojeibane | 623/1 |
| 6,048,361 A | 4/2000 | Von Oepen | 623/1 |
| 6,056,775 A | 5/2000 | Borghi et al. | 623/1.16 |
| 6,068,655 A | 5/2000 | Seguin et al. | 623/1 |
| 6,086,611 A | 7/2000 | Duffy et al. | 623/1 |
| 6,129,754 A | 10/2000 | Kanesaka et al. | 623/1 |
| 6,159,238 A | 12/2000 | Killion et al. | 623/1.11 |
| 6,183,509 B1 | 2/2001 | Dibie | 623/1.35 |
| 6,258,116 B1 | 7/2001 | Hojeibane | 623/1.16 |
| 6,325,826 B1 | 12/2001 | Vardi et al. | 623/1.35 |
| 6,488,702 B1 * | 12/2002 | Besselink | 623/1.15 |
| 6,645,242 B1 | 11/2003 | Quinn | 623/1.16 |
| 6,709,440 B2 | 3/2004 | Callol et al. | 606/108 |
| 6,945,992 B2 | 9/2005 | Goodson, IV et al. | 623/1.13 |
| 6,964,681 B2 | 11/2005 | Murray, III | 623/1.15 |
| 2001/0056298 A1 | 12/2001 | Brown et al. | 623/1.16 |
| 2002/0007212 A1 | 1/2002 | Brown et al. | 623/1.16 |
| 2003/0191523 A1 | 10/2003 | Hojeibane | |
| 2003/0212450 A1 | 11/2003 | Schlick | 623/1.15 |
| 2004/0186556 A1* | 9/2004 | Hogendijk et al. | 623/1.16 |
| 2005/0182473 A1 | 8/2005 | Eidenschink et al. | 623/1.11 |
| 2005/0192656 A1 | 9/2005 | Eidenschink | 623/1.11 |
| 2005/0273149 A1 | 12/2005 | Tran et al. | 623/1.11 |
| 2006/0074476 A1 | 4/2006 | Holman et al. | 623/1.11 |

FOREIGN PATENT DOCUMENTS

EP 0 335 341 B1 10/1989
EP 1 110 515 A2 6/2001

OTHER PUBLICATIONS

U.S. Appl. No. 11/273,186, filed Nov. 14, 2005, Eidenschink et al.

* cited by examiner

Primary Examiner—Sam Chuan C Yao
Assistant Examiner—Kevin Everage
(74) Attorney, Agent, or Firm—Vidas, Arrett & Steinkraus

(57) ABSTRACT

A stent that has a middle section is that is engaged to the proximal section and the distal section by rotational links which extend about the circumference of the stent. The reduced diameters of the proximal section and the distal section are smaller than the reduced diameter of the middle section.

24 Claims, 25 Drawing Sheets

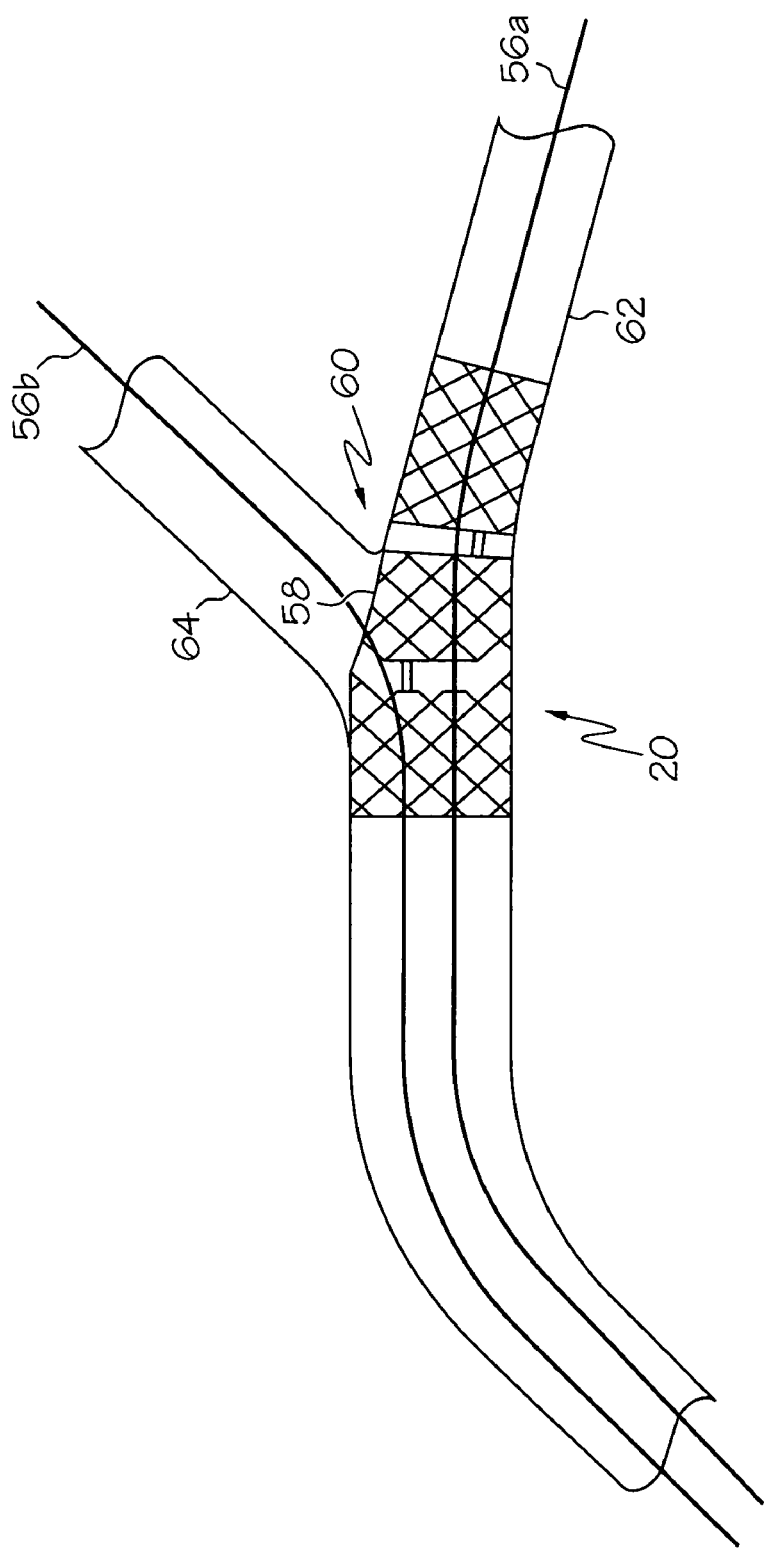

STENT WITH VARIABLE CRIMPING DIAMETER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially reduced configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent with three sections, a proximal section, a middle section and a distal section. Each section has at least one circumferential ring. A rotational link engages the proximal section to the middle section and a rotational link engages the middle section to the distal section. The three sections of the stent have a non-reduced diameter and a reduced diameter. The reduced diameter of the middle section is greater than either the reduced diameter of the proximal section or the distal section. The reduced diameter of the proximal section may be equal to or different from the reduced diameter of the distal section. When the stent is crimped onto a catheter assembly, the two rotational links allow the middle section to rotate about the catheter assembly while the proximal section and the distal section of the stent are engaged to the catheter assembly.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 6b is a flat view of an alternate embodiment of the stent in FIG. 6a.

FIG. 6c is a flat view of an alternate embodiment of the stent in FIG. 6a.

FIG. 6d is a flat view of an alternate embodiment of the stent in FIG. 6a.

FIG. 7b is a flat view of an alternate embodiment of the stent in FIG. 7a.

FIG. 7c is a flat view of an alternate embodiment of the stent in FIG. 7a.

FIG. 7d is a flat view of an alternate embodiment of the stent in FIG. 7a.

FIG. 8b is a flat view of an alternate embodiment of the stent in FIG. 8a.

FIG. 8c is a flat view of an alternate embodiment of the stent in FIG. 8a.

FIG. 8d is a flat view of an alternate embodiment of the stent in FIG. 8a.

FIG. 9b is a flat view of an alternate embodiment of the stent in FIG. 9a.

FIG. 9c is a flat view of an alternate embodiment of the stent in FIG. 9a.

FIG. 9d is a flat view of an alternate embodiment of the stent in FIG. 9a.

FIG. 10d is a view of the embodiment in FIG. 10a in an expanded state within the vessel at the point of a bifurcation.

DETAILED DESCRIPTION OF THE INVENTION

Figure 1:
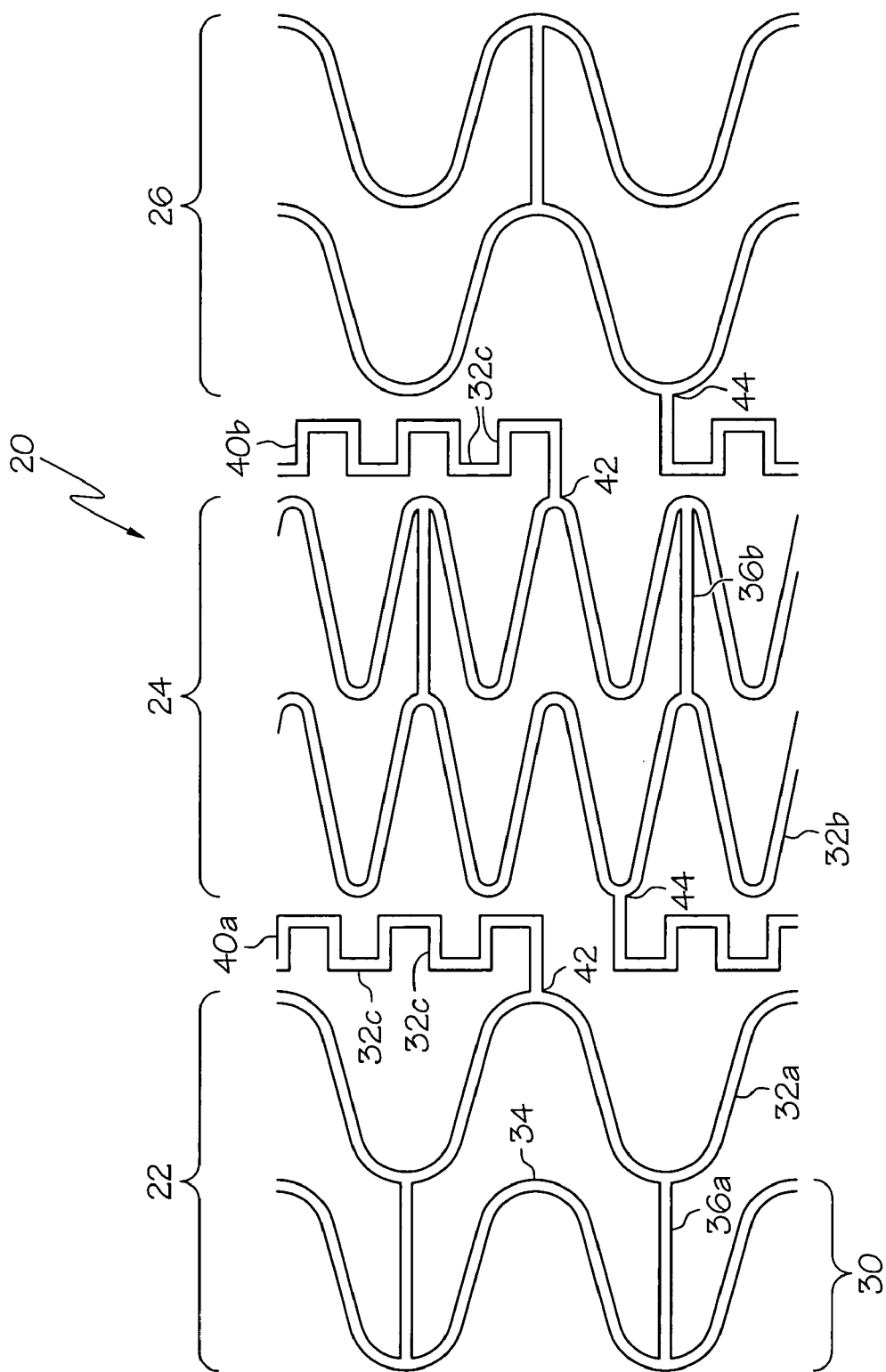
FIG. 1 is a flat view of an embodiment of the inventive stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of the inventive stent in a flat view. The stent has a proximal section 22, a middle section 24, a distal section 26 and two rotational links 40a and 40b. The proximal section 22, the middle section 24 and the distal section 26 have at least one circumferential ring 30 composed of a plurality of struts 32a,b.

In this embodiment, each section 22, 24, and 26 has two circumferential rings 30. It is within the scope of the invention for each section 22, 24, 26 to have one, two, three, four, five, six or more circumferential rings 30. It is also within the scope of the invention for each section 22, 24, and 26 to have different numbers of circumferential rings 30, or for the middle section 24 to have different number of circumferential rings 30 than the proximal section 22 and the distal section 26. Circumferential rings 30 within a section are engaged to each other by connecting struts 36a,b. In this embodiment, the struts 32a,b and turns 34 of the circumferential ring 30 form a serpentine or wave pattern and the circumferential rings 30 of a particular section are in phase. When circumferential rings 30 are in phase, the turns 34 of those circumferential rings 30 correlate with one another so that the turns 34 are in the same direction, thereby forming a synchronized pattern. Thus for example, all the turns 34 at a particular circumferential location extend in one direction, e.g. distally, and all the turns 34 at the adjacent circumferential location extend in a different location, e.g. proximally. It is within the scope of the invention for the struts 32a,b and turns 34 of the circumferential ring 30 to form any pattern. In addition, the circumferential rings 30 of the proximal section 22 are in phase with the circumferential rings 30 of the distal section 26.

The proximal end 42 of the first rotational link 40a is engaged to the proximal section 22. The distal end 44 of the first rotational link 40a is engaged to the middle section 24. The proximal end 42 of the second rotational link 40b is engaged to the middle section 24. The distal end 44 of the second rotational link 40b is engaged to the distal section 26. In this embodiment, the first and second rotational links 40a and 40b are a serpentine pattern but it is within the scope of the invention for the rotational links to be any pattern, for example, but not limited to loops, spirals or curls. In addition, in this embodiment, both the first and second rotational links 40a and 40b are in phase with one another.

Figure 2:
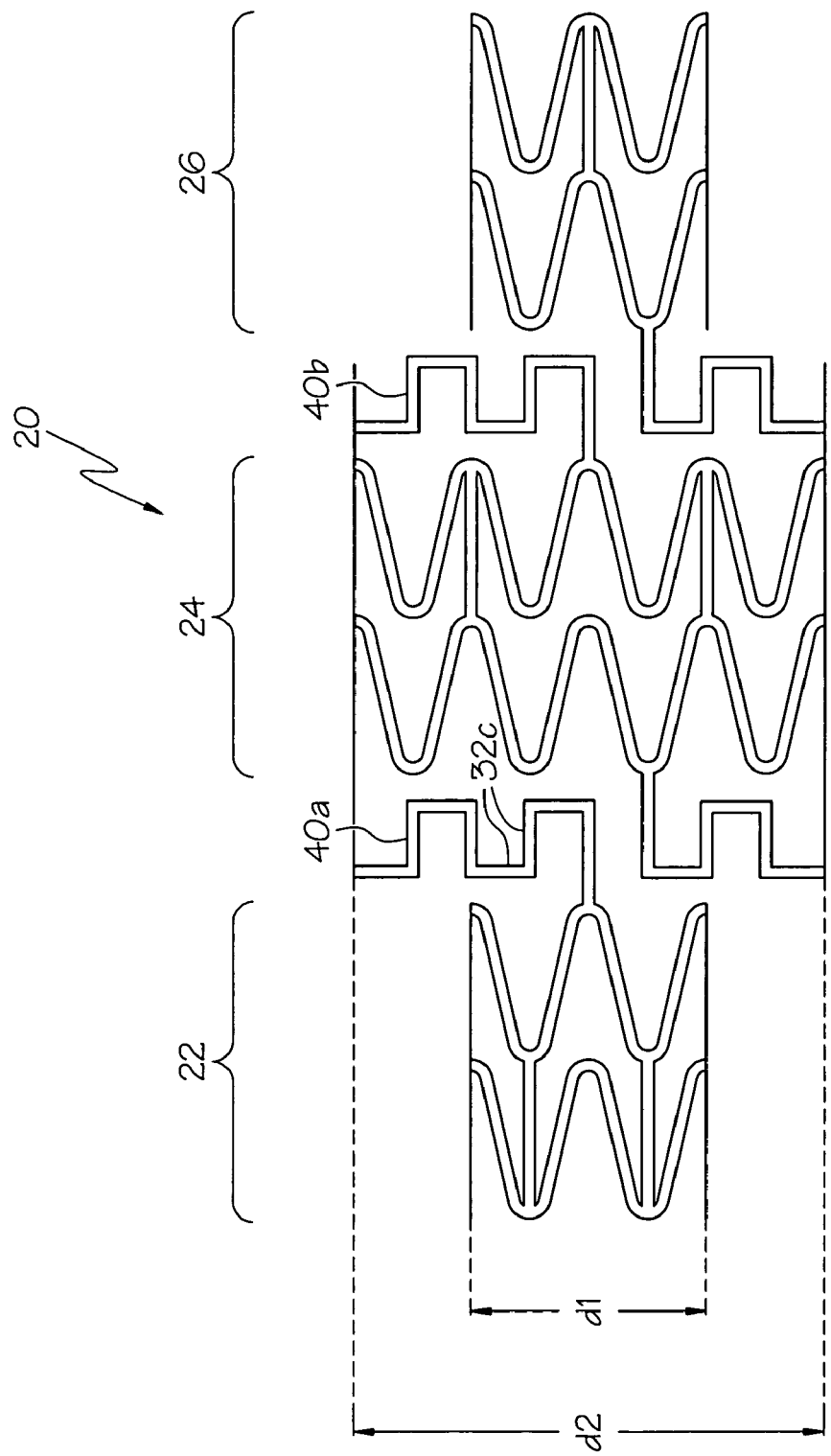
FIG. 2 is a side view of the stent in FIG. 1 where the stent is in a reduced state.

As shown in FIGS. 1 and 2, the first rotational link 40a is composed of a plurality of struts 32c. The first rotational link 41 extends circumferentially in a counter clock-wise direction from the proximal end 42 engaged to a turn 34 on the proximal section 22 to the distal end 44 engaged to a turn 34 on the middle section 24. The turn 34 on the proximal section 22 and the turn 34 on the middle section 24 are adjacent and circumferentially offset from one another with no intervening turns 34. The second rotational link 40b also extends circumferentially in a counter clockwise direction from the proximal end 42, engaged to a turn 34 on the middle section 24, to the distal end 44 engaged to a turn on the distal section 26. The proximal ends 42 of the rotational links 40a and 40b are located at different longitudinal positions but at the same circumferential position. The distal ends 44 of the rotational links 40a and 40b are located at different longitudinal positions and substantially the same circumferential position. Thus, in this embodiment, the rotational links 40a,b extend about a substantial portion of the circumference of the stent 20. In all embodiments described herein, it is within the scope of the invention for a rotational link 40 to extend about the circumference of the stent 20 in either a clockwise direction or a counter clockwise direction.

Figure 3B:
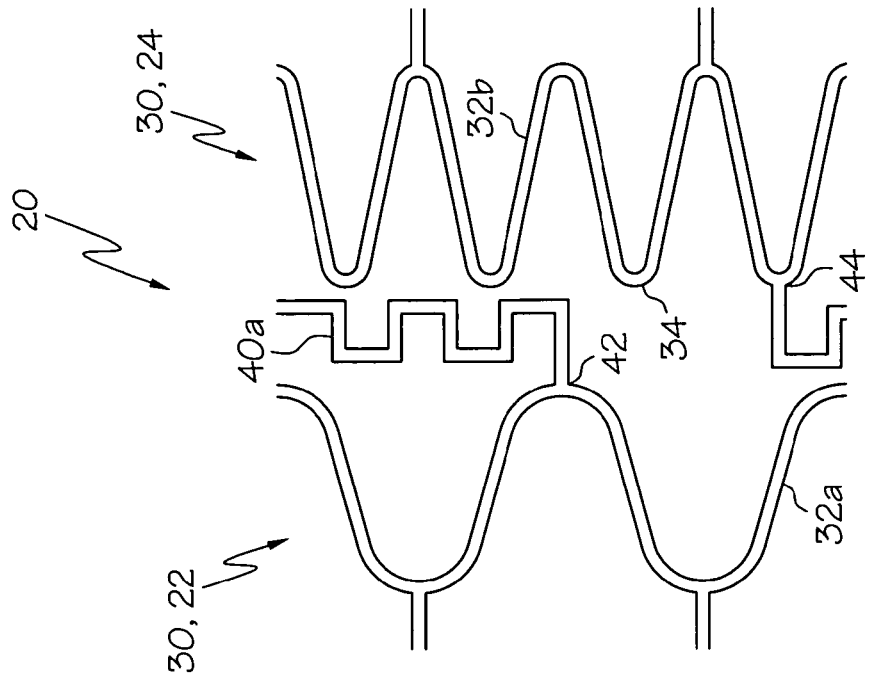
FIG. 3b is a flat view of an embodiment of the rotational link, where the rotational link extends about a portion of the circumference of the stent.
Figure 3A:
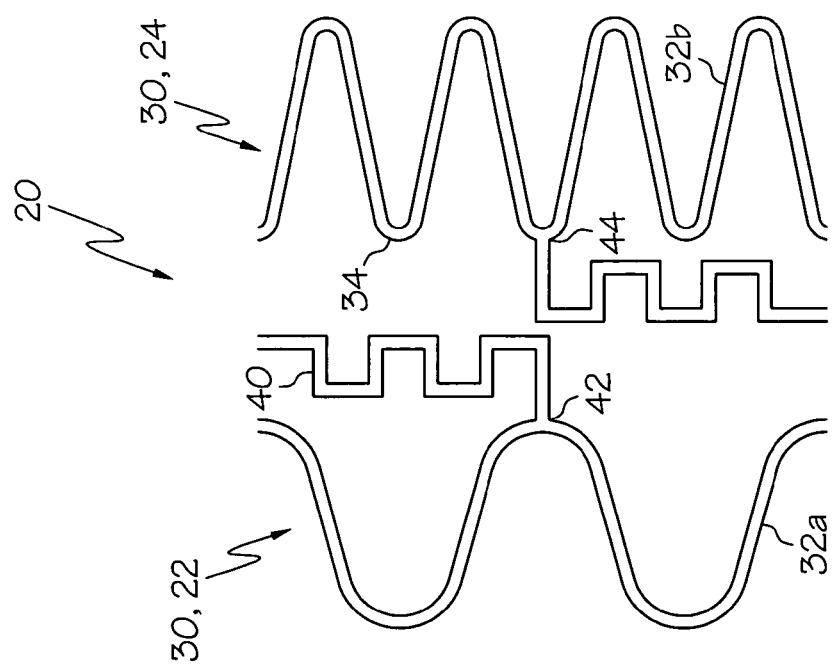
FIG. 3a is a flat view of an embodiment of the rotational link, where the rotational link extends about the entire circumference of the stent.

FIG. 3a shows an embodiment where the rotational link 40 extends about the entire circumference of the stent 20. The proximal end 42 of the rotational link 40 and the distal end 44 of the rotational link 40 have substantially the same circumferential position. This embodiment provides the middle section 24 with the greatest amount of axial rotation relative to the proximal section 22 and the distal section 26. The rotational link 40 in this embodiment extends around the stent 20 in a counter clockwise direction.

A smaller amount of axial rotation can be achieved in many ways, for example, but not limited to altering the circumferential distance between the proximal ends 42 and the distal ends 44 of the rotational links 40a and 40b, to place the proximal ends 42 at different circumferential positions or place the distal ends 44 at different circumferential positions. However, to provide the desired rotational ability, the rotational link 40a,b must extend at least two thirds the way around the circumference of the stent 20. In one embodiment, the circumferential distance between the proximal end 42 and the distal end 44 can be increased. Thus, there would be at least one intervening turn 34 between the turn 34 to which the proximal end 42 of the rotational link 40a,b is engaged and the turn 34 to which the distal end 44 of the rotational link 40a,b is engaged. The at least one intervening turn 34 is not adjacent to the rotational link 40a,b, unlike the other turns 34 of both the proximal section 22 and the middle section 24. This alternate embodiment of the rotational link 40a can be seen in FIG. 3b where the circumferential distance between the proximal end 42 and the distal end 44 of the rotational link 40a is greater than in FIG. 1.

In one embodiment, the proximal ends 42 of the rotational links 40a and 40b have different circumferential positions from one another. In one embodiment, the distal ends 44 of the rotational links 40a and 40b have different circumferential positions from one another.

Figure 4:
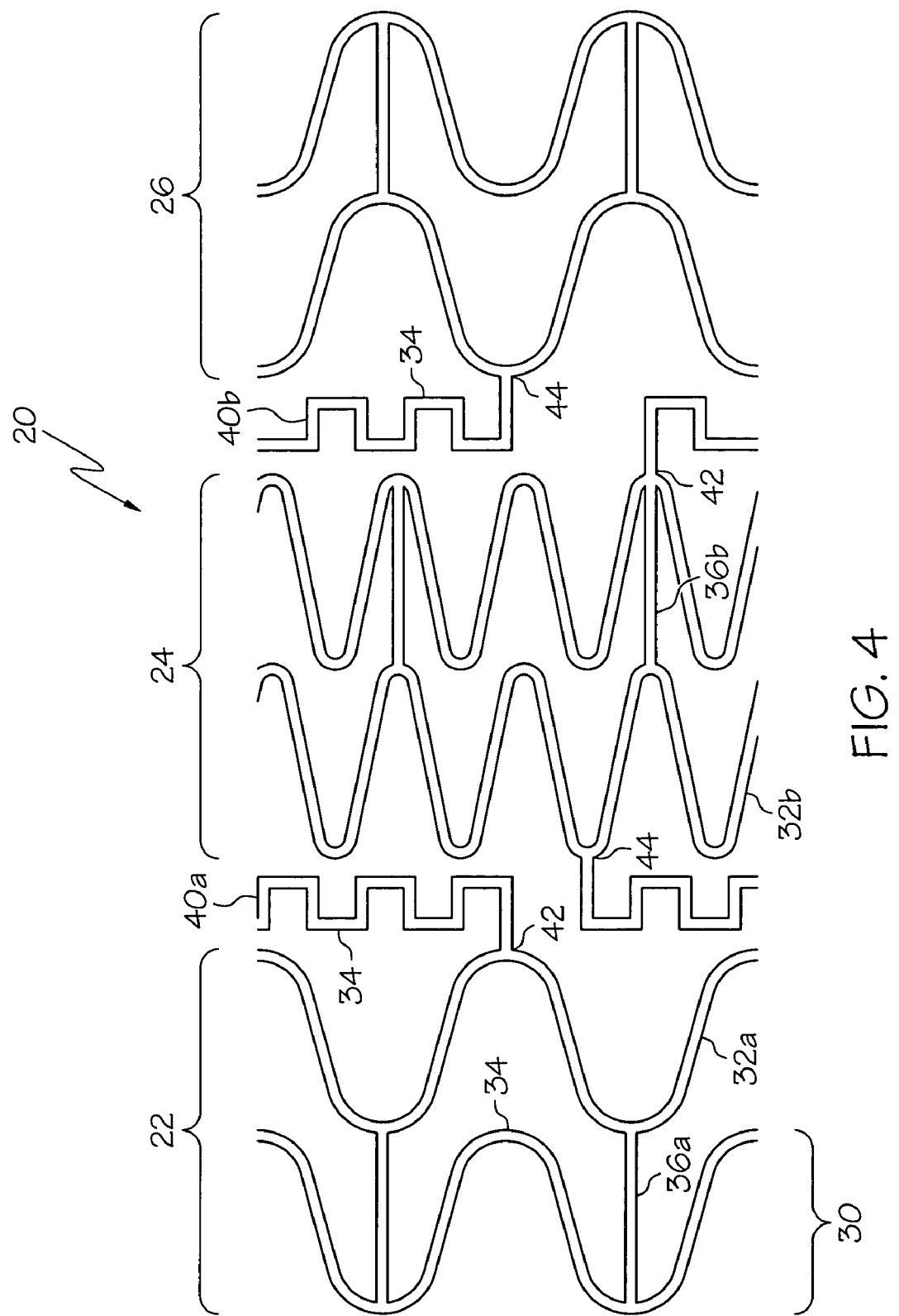
FIG. 4 is a flat view of an embodiment of the stent.

It is within the scope of the invention for the circumferential rings 30 of a particular section 22, 24 or 26 to be out of phase with one another or for the circumferential rings 30 of the proximal section 22 to be out of phase with the circumferential rings 30 of the distal section 26. FIG. 4 shows another embodiment of the stent 20 where the circumferential rings 30 of the proximal section 22 and the distal section 26 are out of phase with one another and the rotational links 40a and 40b are out of phase with one another. Therefore, turns 34 of the respective circumferential rings 30 and/or rotational links 40a,b at the same circumferential position are 180 degrees out of phase with one another. Thus, the turn 34 of one circumferential ring 30 extends one direction, e.g. proximally, while the turn 34 of the adjacent circumferential ring 30 extends in the opposite direction, e.g. distally. In addition, the first and second rotational links 40a and 40b extend in different directions about the circumference of the stent 20. The first rotational link 40a extends circumferentially from the proximal end 42 to the distal end 44 in a counter clockwise direction. The second rotational link 40b extends circumferentially from the proximal end 42 to the distal end 44 in a clockwise direction.

Figure 5:
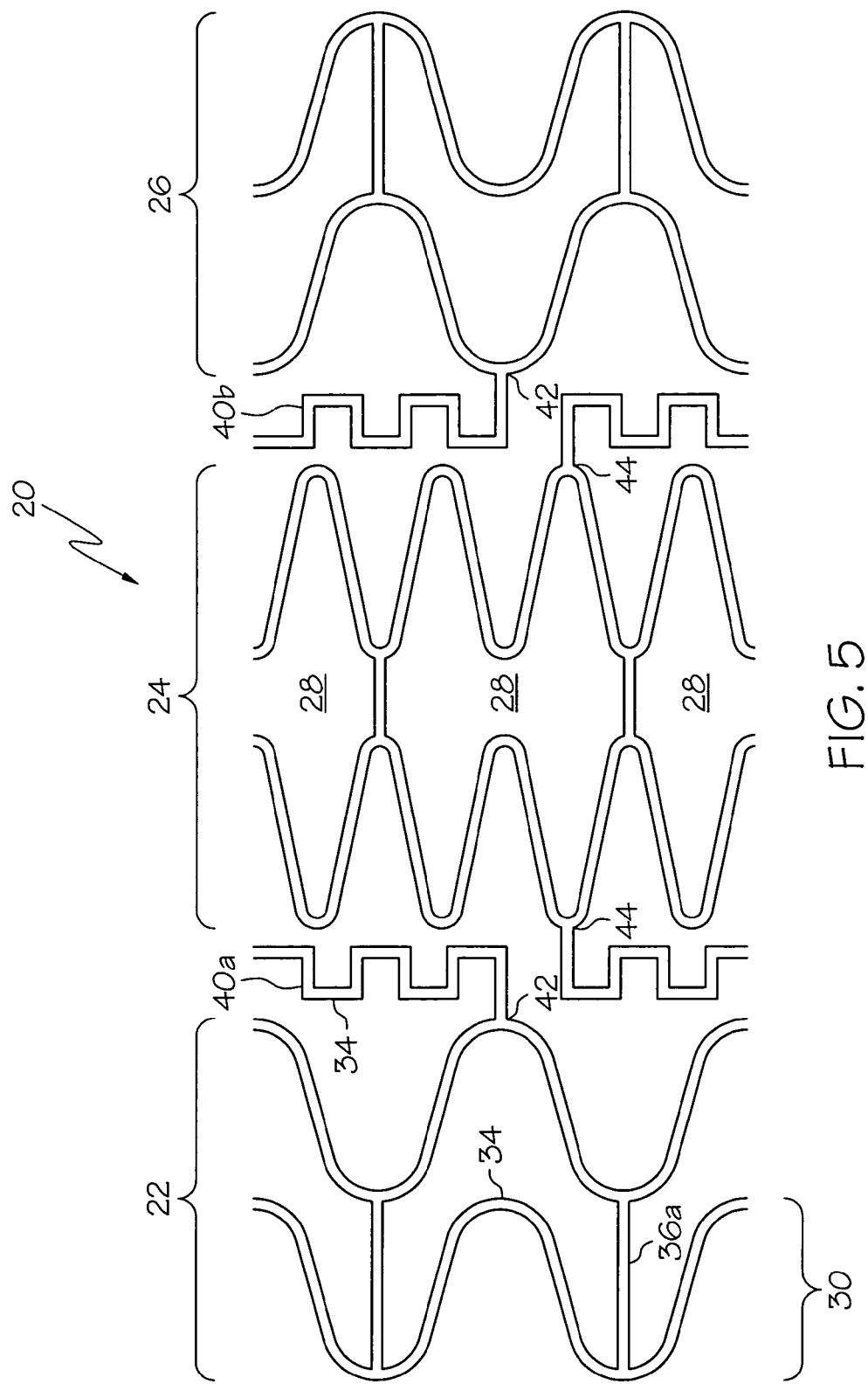
FIG. 5 is a flat view of an embodiment of the stent.

FIG. 5 shows an additional embodiment of the stent 20 where several components of the stent 20 are out of phase with one another. In this embodiment, the proximal section 22 is out of phase with the distal section 26, the circumferential rings 30 of the middle section 24 are out of phase with one another and the rotational links 40a and 40b are out of phase with one another. The rotational links 40a and 40b also extend circumferentially from the proximal ends in different directions, the first rotational link 40a extending in a counter clockwise direction and the second rotational link 40b extending in a clockwise direction.

Figure 6A:
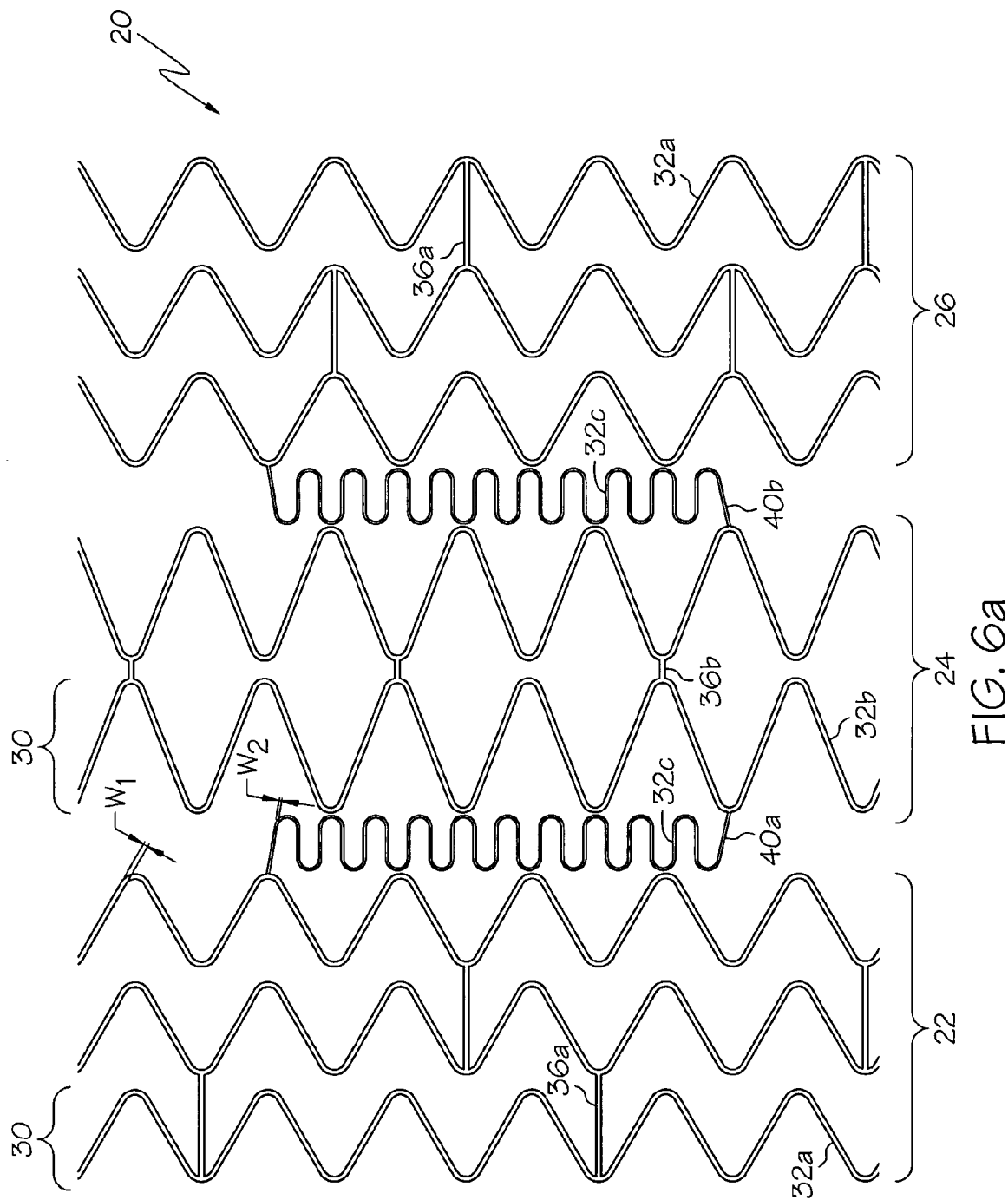
FIG. 6a is a flat view of an embodiment of the stent where the struts of the middle section have a greater length than the struts of both the proximal section and the distal section.
Figure 6B:
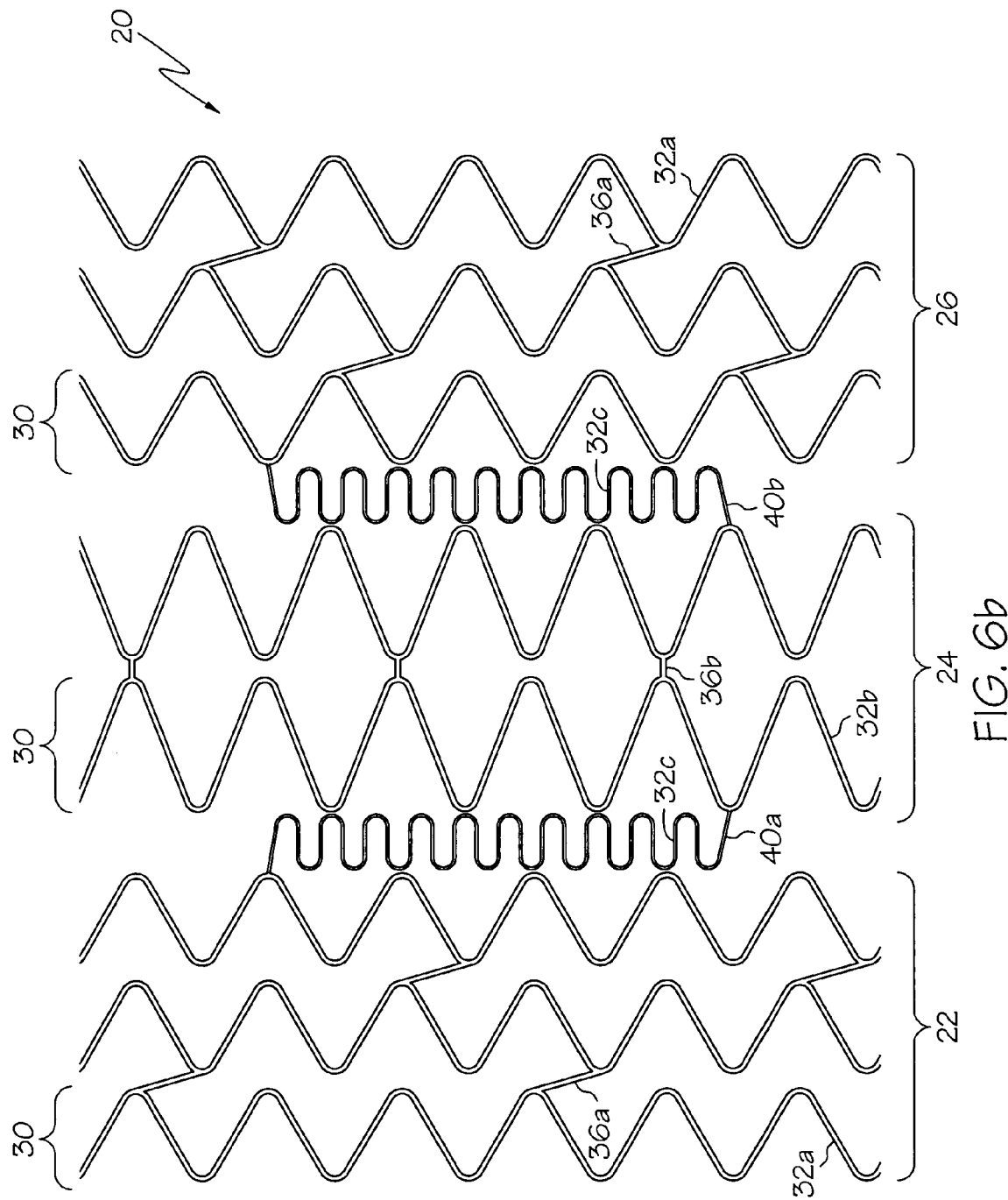
Figure 6C:
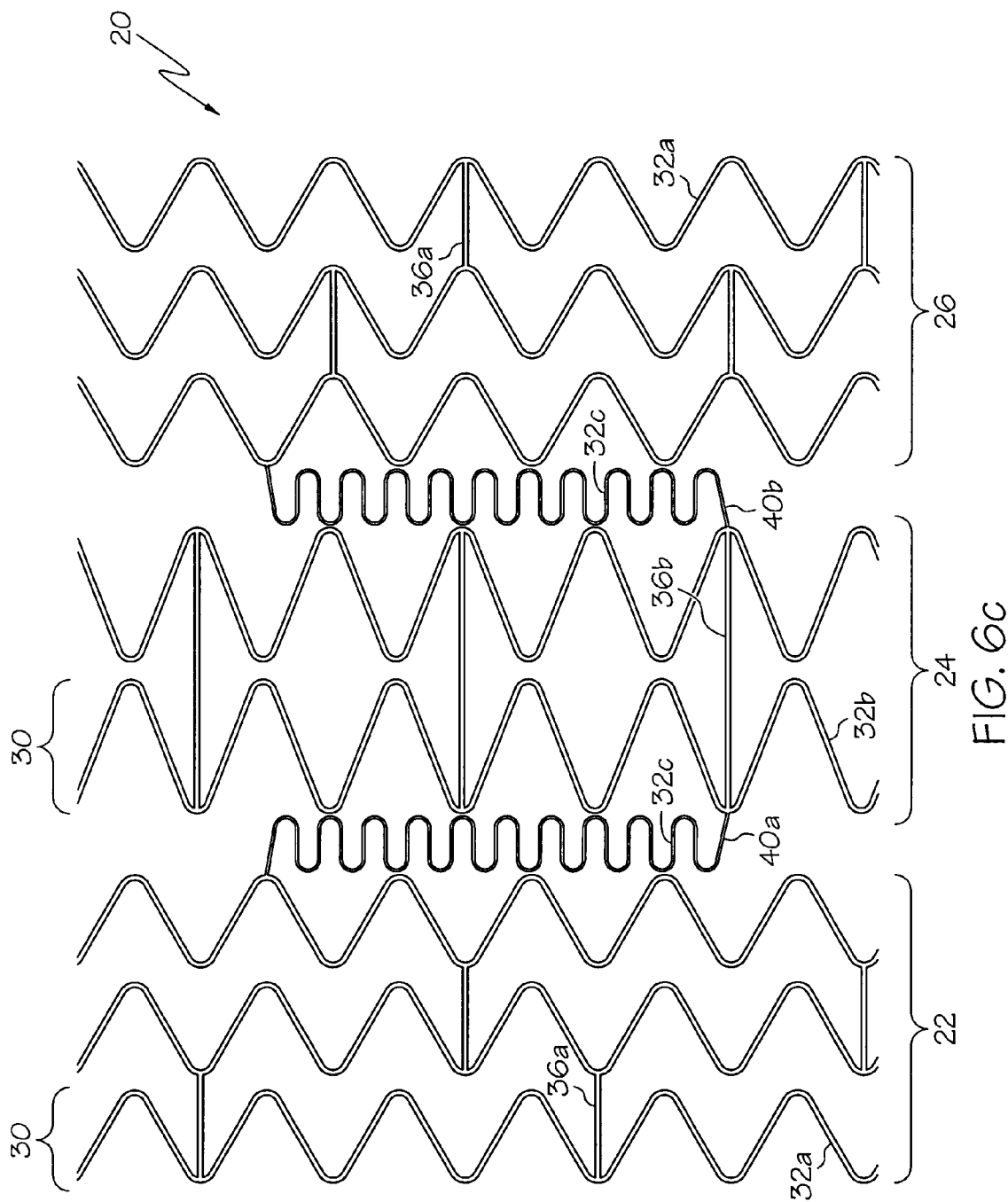
Figure 6D:
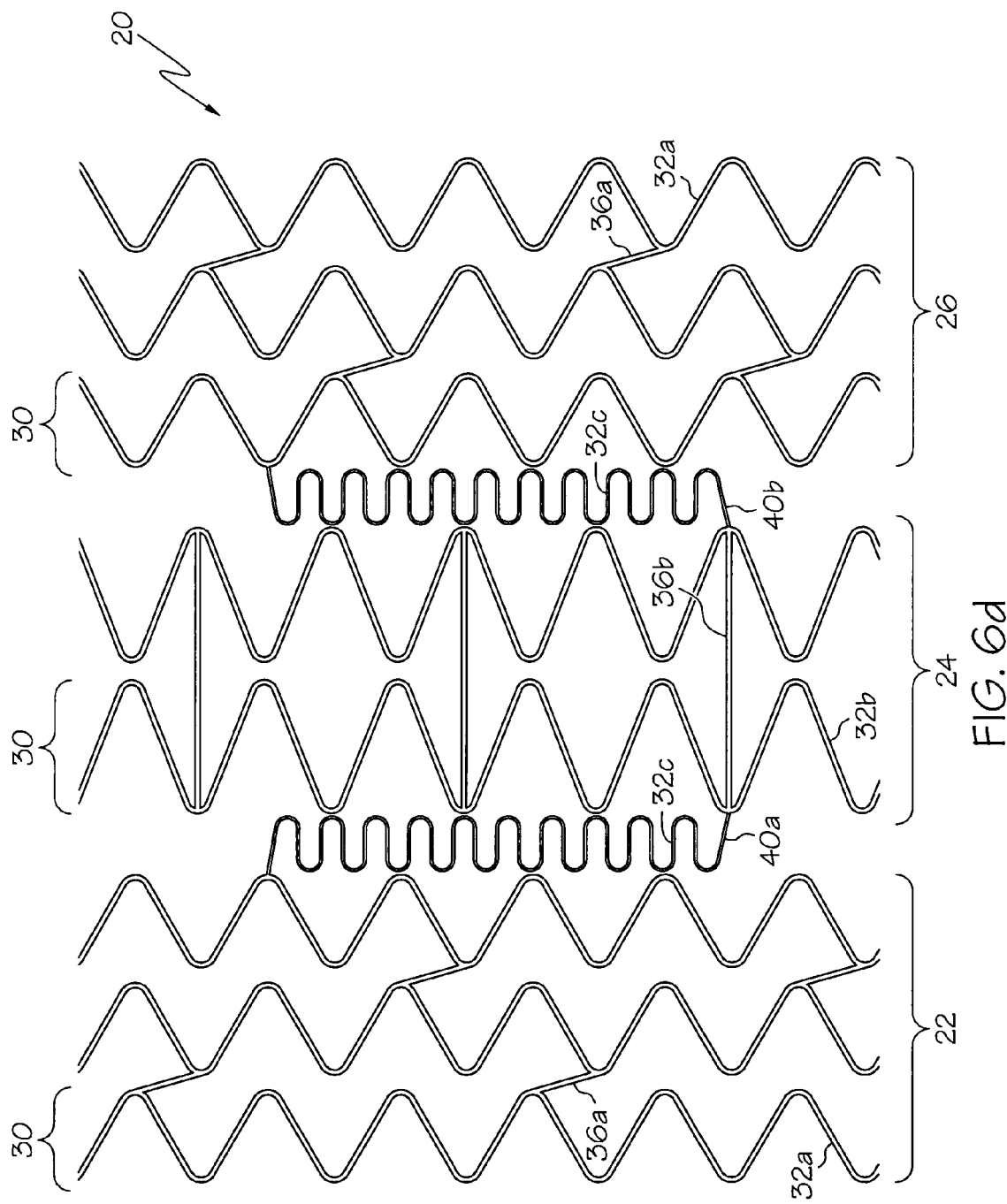

FIG. 6a is another embodiment of the stent 20 with FIGS. 6b-6d showing alternative embodiments the FIG. 6a embodiment. The embodiment in FIG. 6a has a proximal section 22, a middle section 24 and a distal section 26 with a rotational link 40a engaging the proximal section 22 to the middle section 24 and a rotational link 40b engaging the middle section 24 to the distal section 26. Note that the width W2 of the struts 32c forming the rotational links 40a,b is smaller than the width W1 of the struts 32a,b forming the proximal section, middle section and the distal section. In addition, the rotational links 40a,b have a higher frequency of struts 32c compared to the frequency of struts 32a,b in the proximal section 22, the middle section 24 and the distal section 26. The frequency of struts 32 depends upon the number of struts 32 in a given circumferential length. The struts 32a of the distal section 22 and the proximal sections 26 have a shorter longitudinal length than the struts 32b of the middle section 24. The circumferential rings 30 of the proximal section 22 and the distal section 26 are in phase with one another while the circumferential rings 30 of the middle section 24 are out-of-phase with one another. In addition, adjacent circumferential rings 30 of the proximal and distal sections 22, 26 are engaged by connectors 36a. The connectors 36a are peak-valley connectors which extend from a peak on one circumferential ring 30 to the valley of the adjacent circumferential ring 30. The middle section 24 also has connectors 36b which are peak-peak connectors which extend from a peak on one circumferential ring 30 to the peak of the adjacent circumferential ring 30.

The embodiment in FIG. 6b differs from the FIG. 6a embodiment in that the connectors 36a of the proximal and distal sections 22,26 are angled peak-peak connectors 36a that extend from a peak on one circumferential ring 30 to a peak on the adjacent circumferential ring 30. Angled connectors 36 are positioned at an oblique angle to the longitudinal axis.

The embodiment in FIG. 6c differs from the FIG. 6a embodiment in that the connectors 36b of the middle section 24 are valley-valley connectors 36b that extend from a valley on one circumferential ring 30 to a valley on the adjacent circumferential ring 30.

The embodiment in FIG. 6d differs from the FIG. 6a embodiment in two ways. First, the connectors 36a of the proximal and distal sections 22,26 are angled peak-peak connectors 36a that extend from a peak on one circumferential ring 30 to a peak on the adjacent circumferential ring 30. Second, the connectors 36b of the middle section 24 are valley-valley connectors 36b that extend from a valley on one circumferential ring 30 to a valley on the adjacent circumferential ring 30.

Figure 7A:
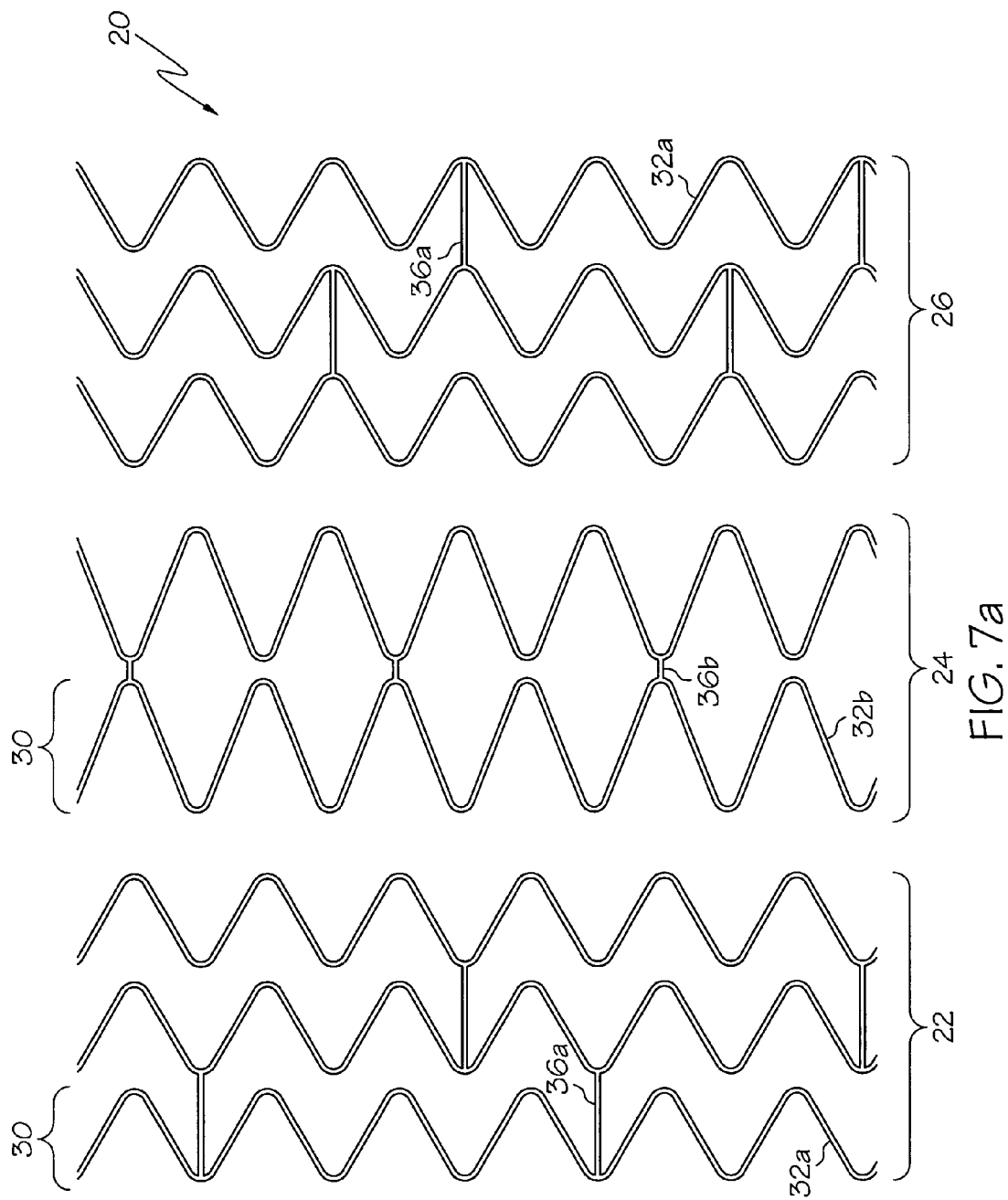
FIG. 7a is a flat view of an embodiment of the stent where the struts of the middle section have a greater length than the struts of both the proximal section and the distal section and there are no rotational links.
Figure 7B:
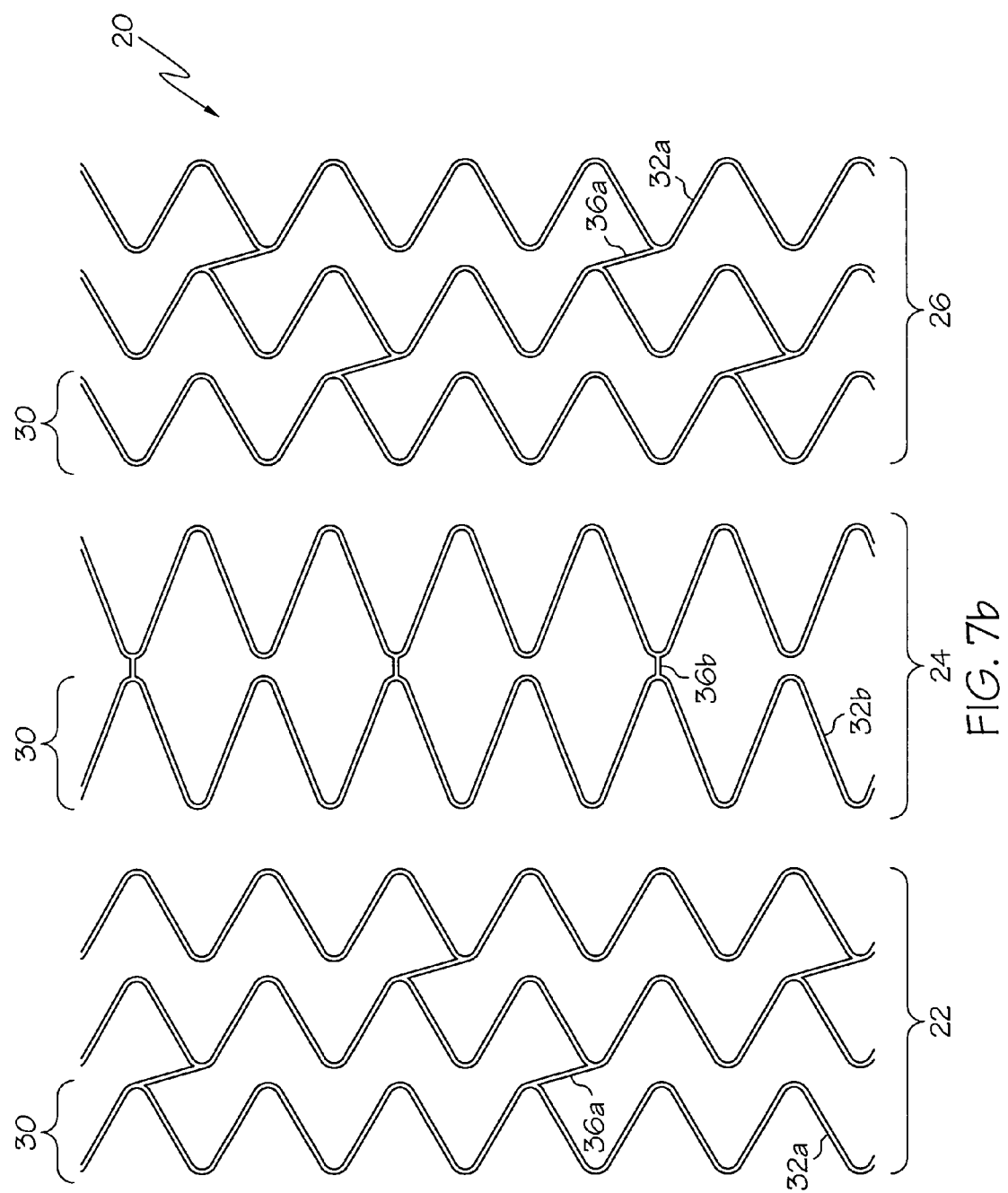
Figure 7C:
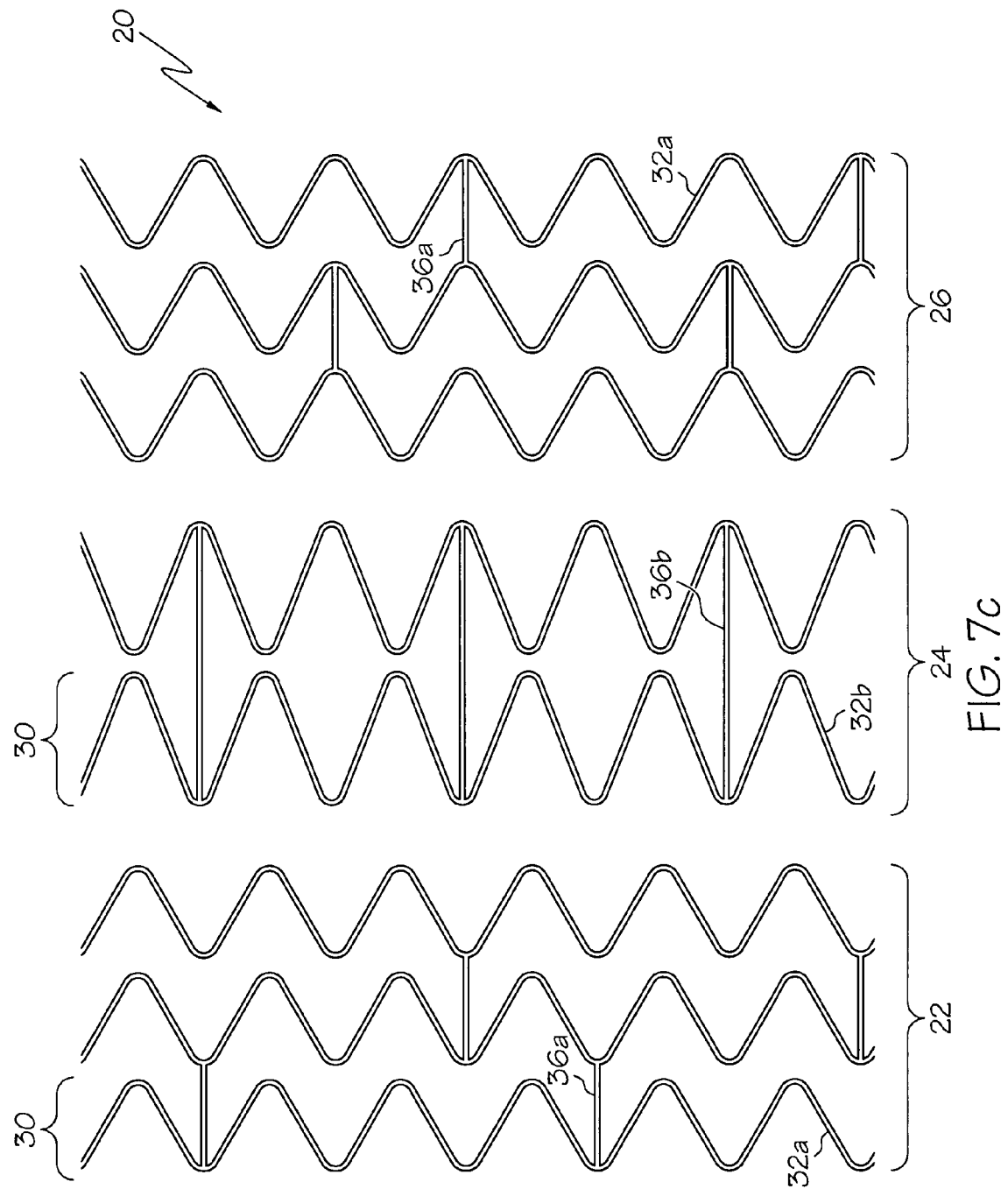
Figure 7D:
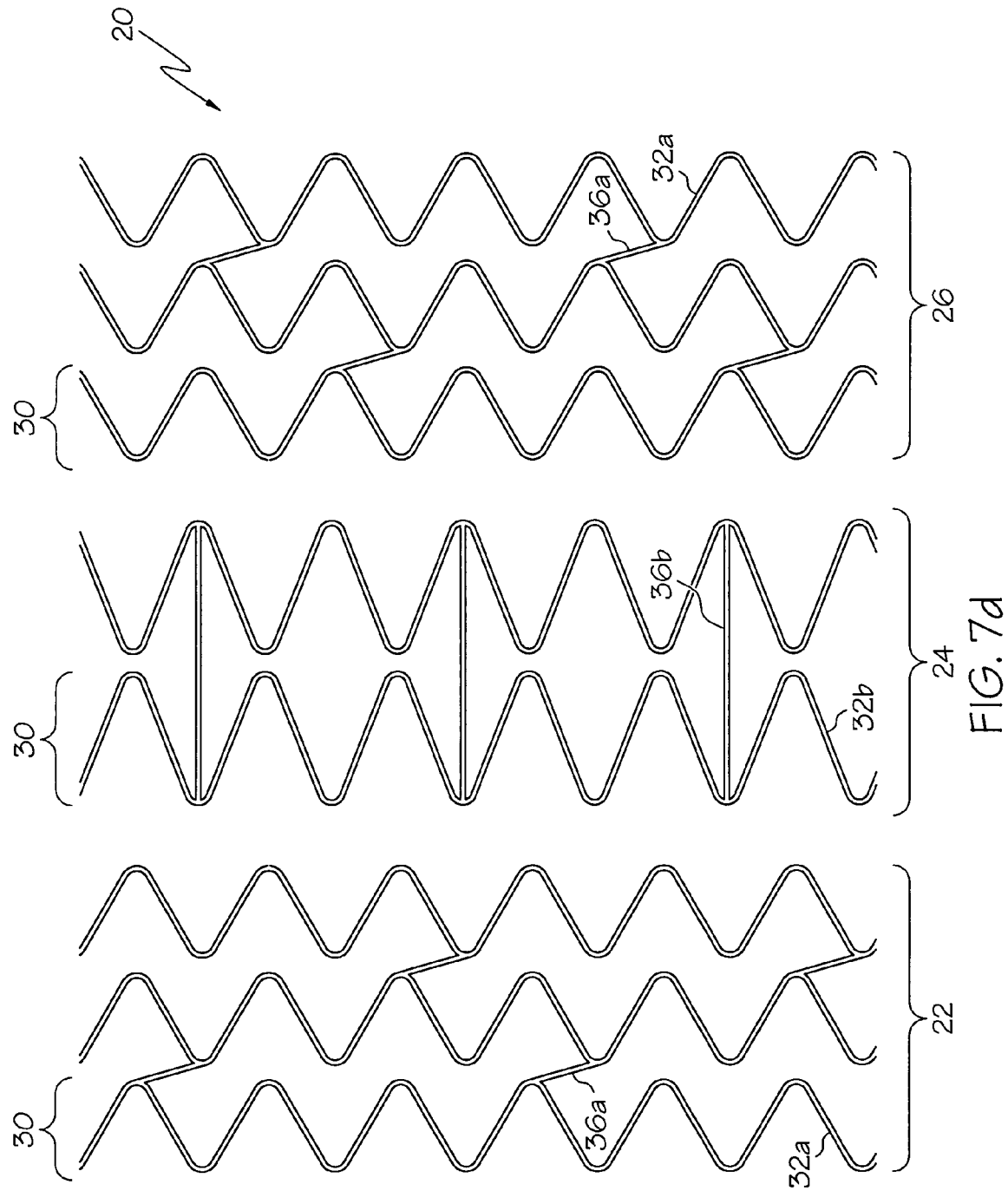

FIG. 7a has another embodiment of the inventive stent 20 with FIGS. 7b-7d showing alternative embodiments the FIG. 7a embodiment. FIG. 7a is the embodiment of FIG. 6a without the rotational links 40a,b. Similarly, FIG. 7b is the embodiment of FIG. 6b without the rotational links 40a,b; FIG. 7c is the embodiment of FIG. 6c without the rotational links 40a,b and FIG. 7d is the embodiment of FIG. 6d without the rotational links 40a,b.

Figure 8A:
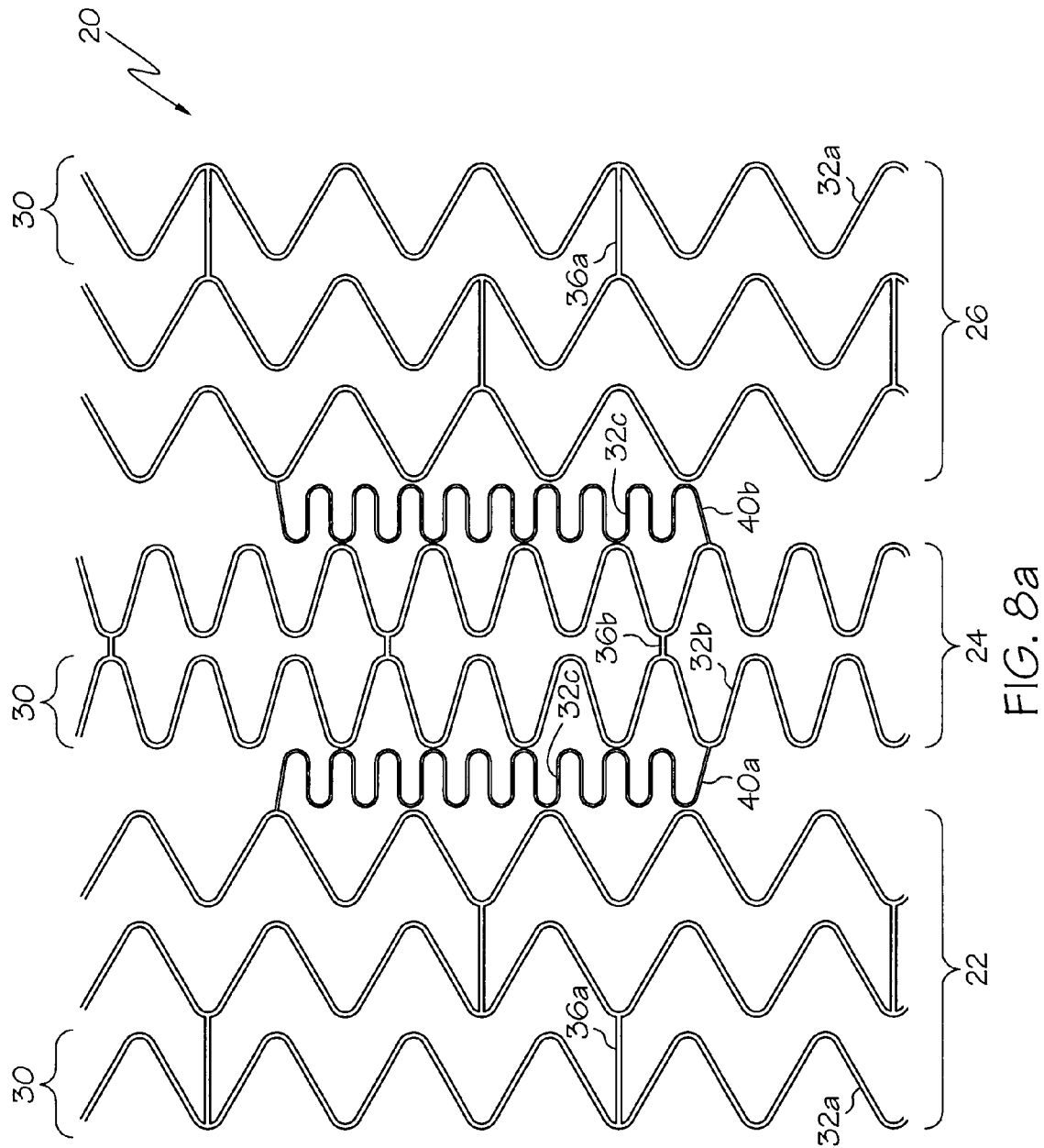
FIG. 8a is a flat view of an embodiment of the stent with rotational links where the middle section has a higher frequency of struts than either the proximal section or the distal section.
Figure 8B:
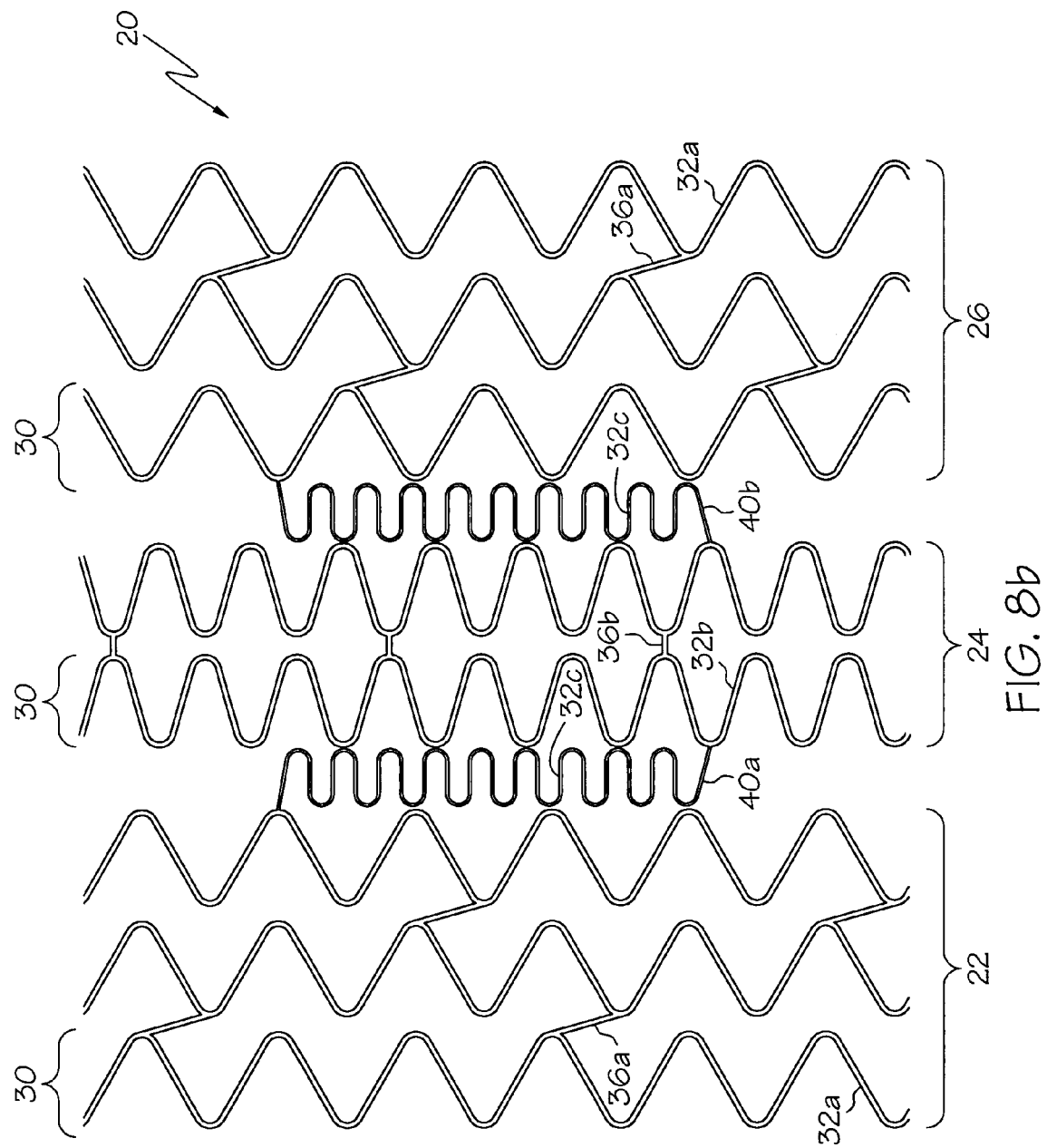
Figure 8C:
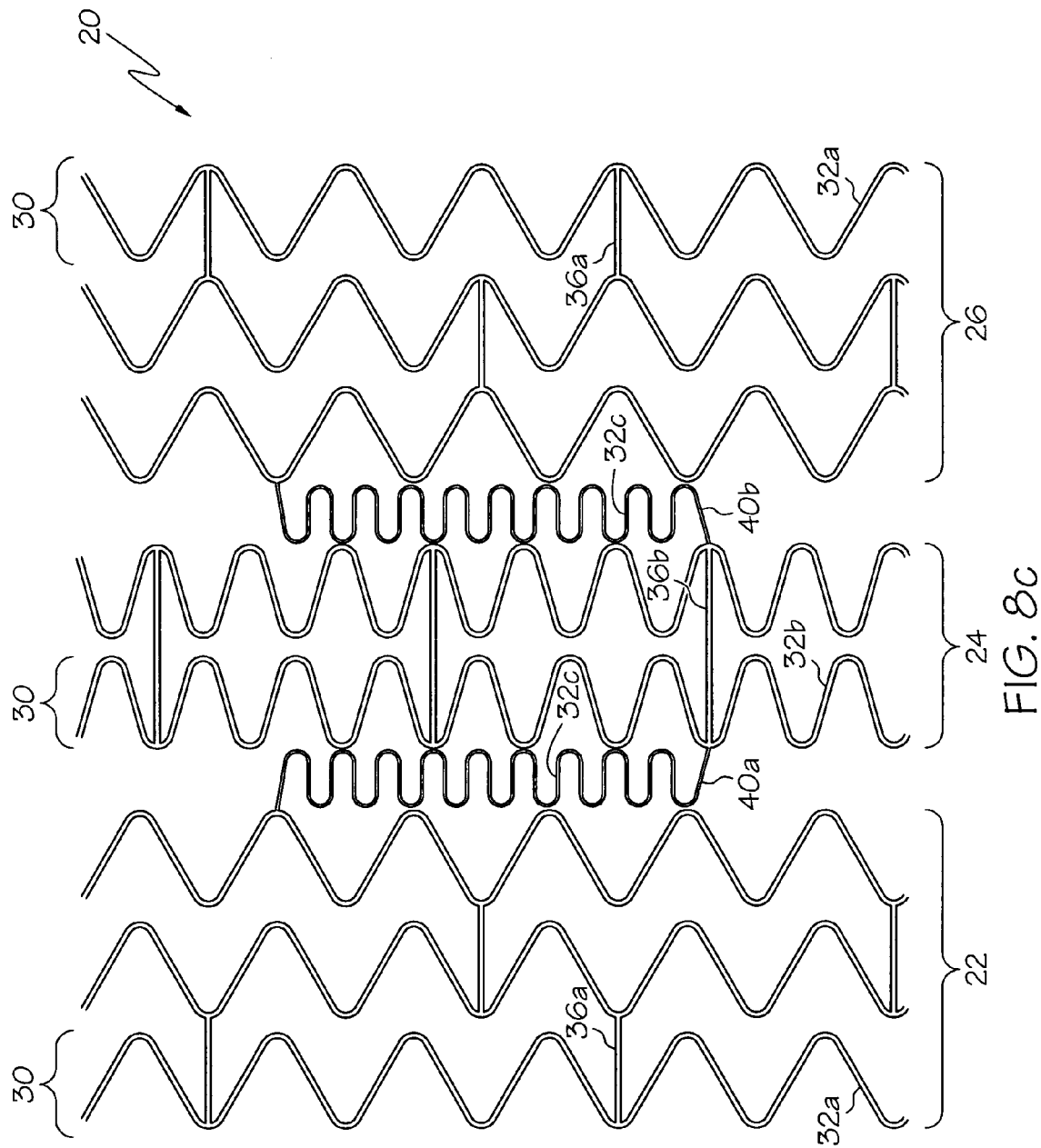
Figure 8D:
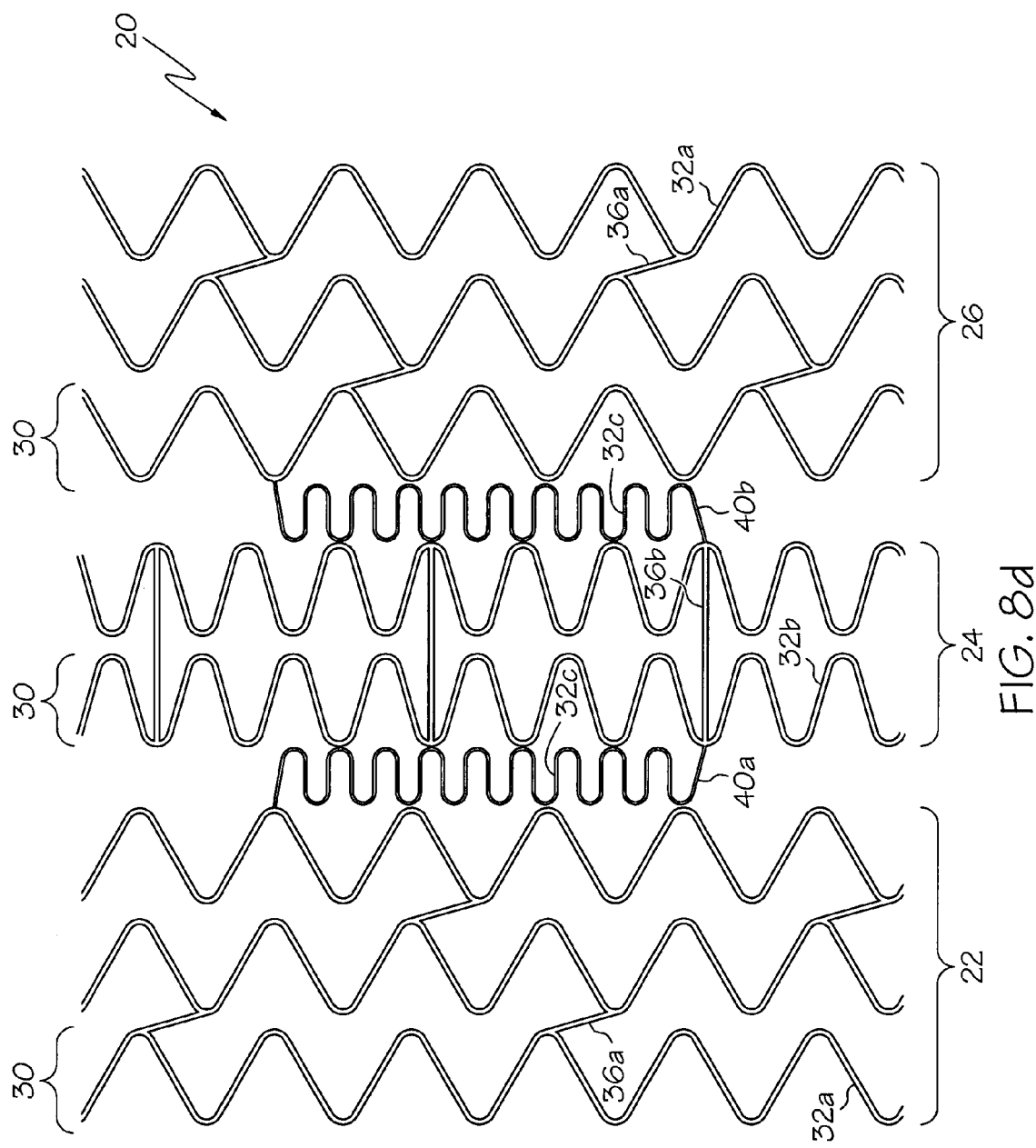

Another embodiment of the inventive stent 20 is illustrated in FIG. 8a with FIGS. 8b-8d showing alternative embodiments of the FIG. 8a embodiment. In the embodiment illustrated in FIG. 8a, the stent 20 has a proximal section 22, a middle section 24 and a distal section 26. The proximal section 22 is engaged to the middle section 24 by a rotational link 40a and the middle section 24 is engaged to the distal section 26 by a rotational link 40b. In this embodiment, the middle section 24 has a higher frequency of struts, i.e. there are a greater number of struts 32b per unit of circumferential ring length in the middle section 24 than either the proximal section 22 or the distal section 26. The circumferential rings 30 of the proximal and distal sections 22, 26 are in phase with one another while the circumferential rings 30 of the middle section are out-of-phase with one another. In addition, the proximal and distal sections 22, 26 have connectors 36a engaging adjacent circumferential rings 30. The connectors 36a are peak-valley connectors which extend from a peak on one circumferential ring 30 to the valley of the adjacent circumferential ring 30. The middle section 24 has connectors 36b which are peak-peak connectors which extend from a peak on one circumferential ring 30 to the peak of the adjacent circumferential ring 30. Note that the middle section 24 has a shorter longitudinal length than either the proximal section 22 or the distal section 26.

The embodiment in FIG. 8b differs from the FIG. 8a embodiment in that the connectors 36a of the proximal and distal sections 22,26 are angled peak-peak connectors 36a that extend from a peak on one circumferential ring 30 to a peak on the adjacent circumferential ring 30.

The embodiment in FIG. 8c differs from the FIG. 8a embodiment in that the connectors 36b of the middle section 24 are valley-valley connectors 36b that extend from a valley on one circumferential ring 30 to a valley on the adjacent circumferential ring 30.

The embodiment in FIG. 8d differs from the FIG. 8a embodiment in two ways. First, the connectors 36a of the proximal and distal sections 22,26 are angled peak-peak connectors 36a that extend from a peak on one circumferential ring 30 to a peak on the adjacent circumferential ring 30. Second, the connectors 36b of the middle section 24 are valley-valley connectors 36b that extend from a valley on one circumferential ring 30 to a valley on the adjacent circumferential ring 30.

Figure 9A:
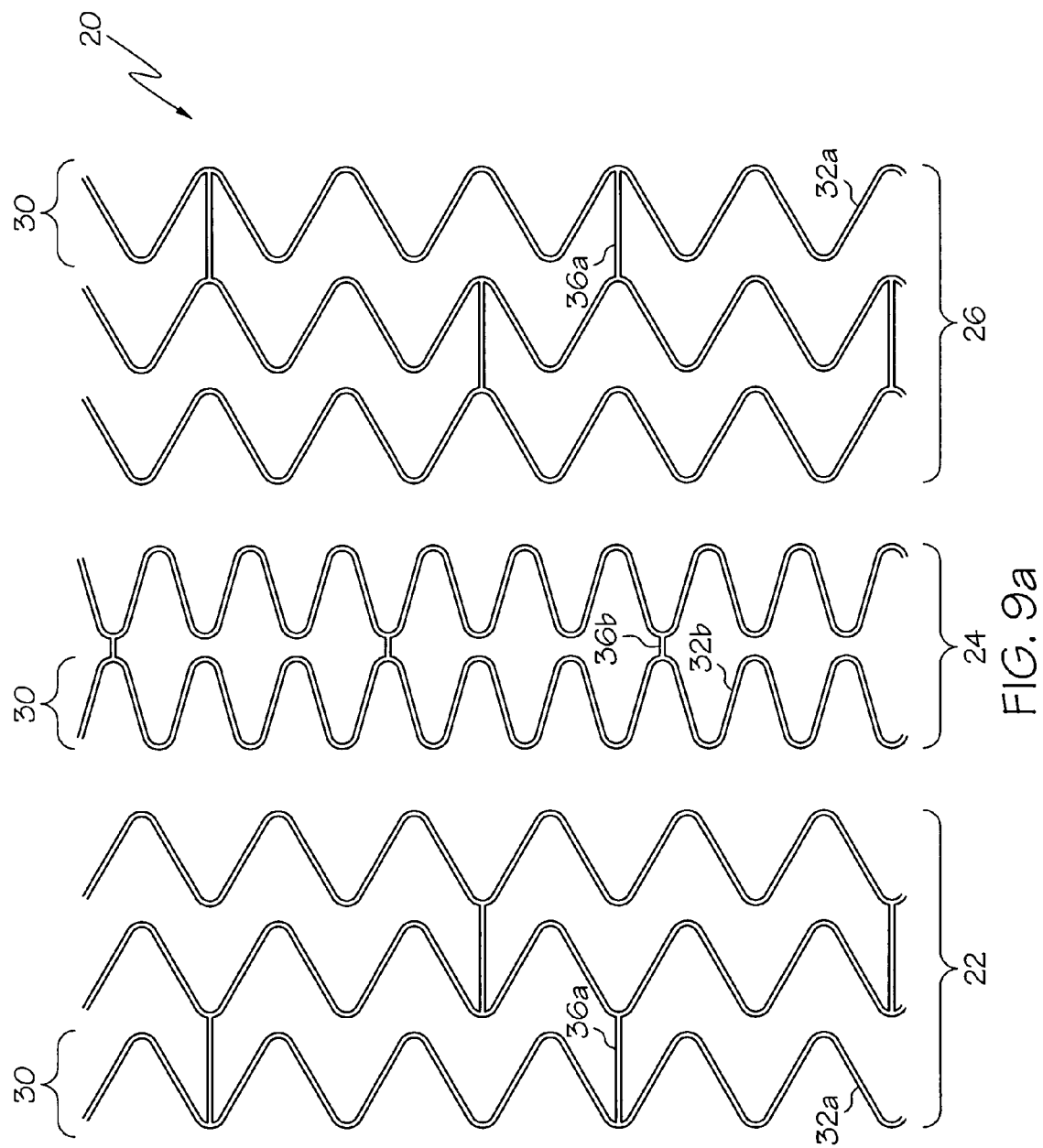
FIG. 9a is a flat view of an embodiment of the stent without rotational links where the middle section has a higher frequency of struts than either the proximal section or the distal section.
Figure 9B:
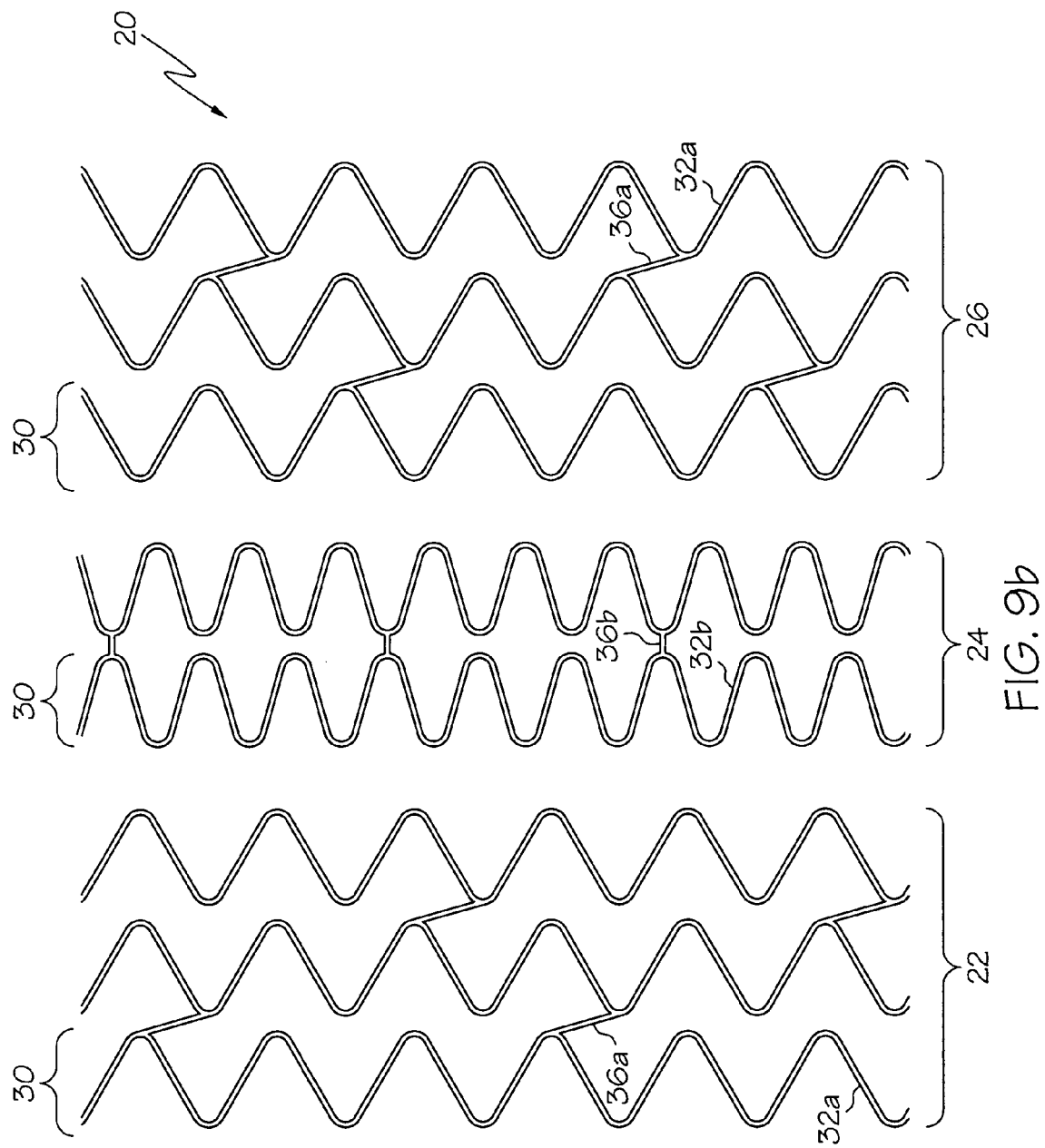
Figure 9C:
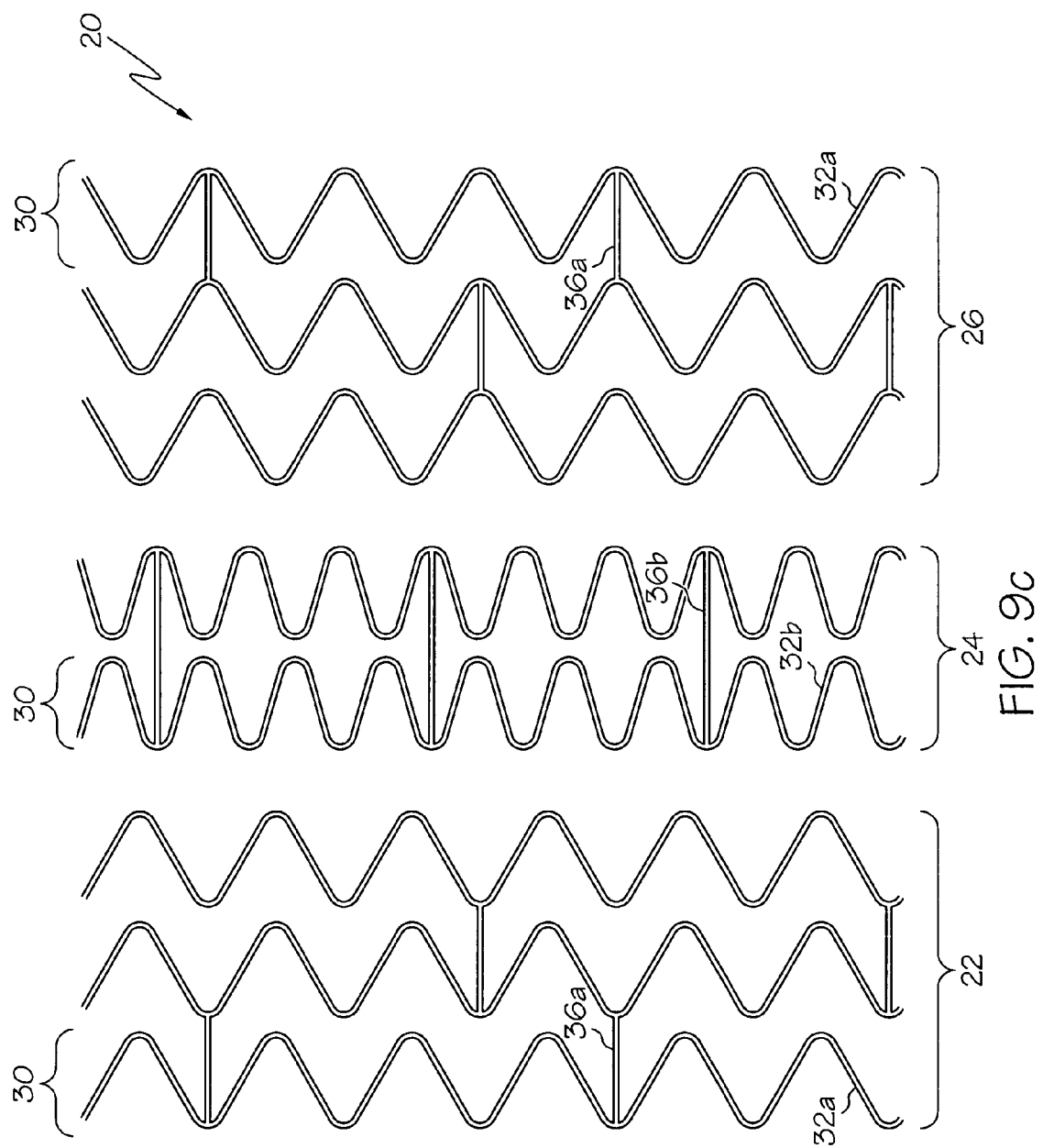
Figure 9D:
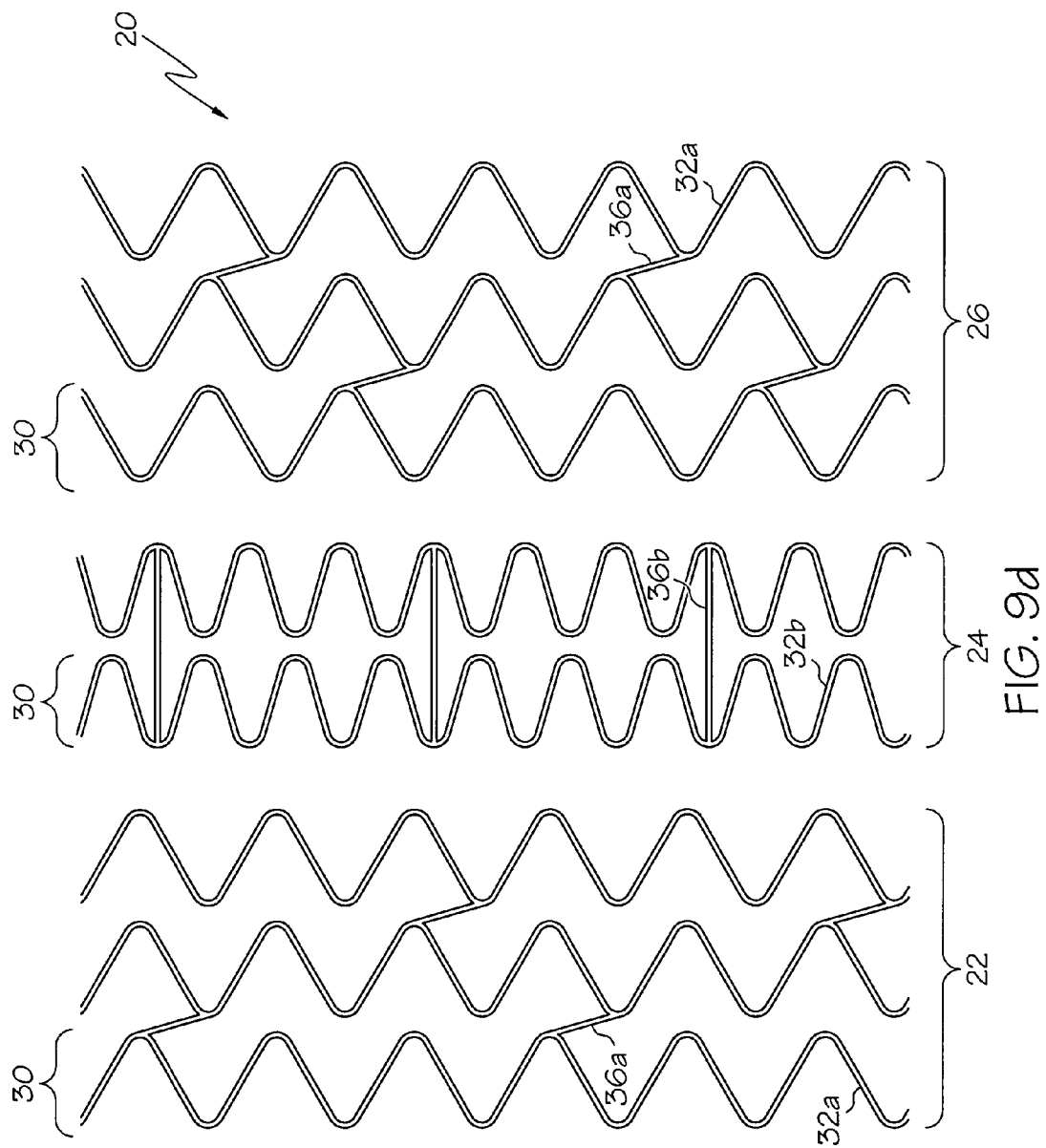

FIG. 9a has another embodiment of the inventive stent 20 with FIGS. 9b-9d showing alternative embodiments the FIG. 9a embodiment. FIG. 9a is the embodiment of FIG. 8a without the rotational links 40a,b. Similarly, FIG. 9b is the embodiment of FIG. 8b without the rotational links 40a,b; FIG. 9c is the embodiment of FIG. 8c without the rotational links 40a,b and FIG. 9d is the embodiment of FIG. 8d without the rotational links 40a,b.

In at least one embodiment, the stent has two sections engaged by a rotational link so that one section rotates axially about the catheter assembly in a reduced state while the other section engages the catheter assembly in a reduced state. In at least one embodiment, the stent has at least one rotatable section and at least one non-rotatable section.

The geometry and corresponding "circumferential weakness" of the rotational link 40 enables the rotation of the middle section 24 relative to the proximal section 22 and the distal section 26. In at least one embodiment, the rotational link 40 has a smaller strut width W2 than the width W1 of the struts 32a,b forming the proximal, middle or distal sections 22,24,26, as illustrated in FIG. 6a. Therefore the struts 32c of the rotational links 40 are thinner than the struts 32a,b of the proximal, middle and distal sections 22,24,26. In at least one embodiment, the thickness of the struts forming the rotational link is less than the thickness of the struts forming the proximal, middle and distal sections. In at least one embodiment, the rotational link 40 has a higher frequency of struts 32c than the frequency of struts 32a,b in the proximal, middle and distal sections 22,24,26, as illustrated in FIG. 6a.

In at least one embodiment, the material used to make the rotational link has a lower material strength than the material used to make the struts of the proximal, middle and distal sections. In at least one embodiment, the rotational link and the proximal, middle and distal sections are made from the same material but the rotational link is heat treated to weaken the strength of the material relative to the proximal, middle and distal sections.

In at least one embodiment, the rotational link has at least one of the following attributes: smaller strut width, higher frequency of struts, a strut thickness less than the strut thickness of the proximal, middle and distal sections, the material used to make the rotational link has a lower material strength than the material used to make the proximal, middle and distal sections, the material used to make the rotational link is the same as that used to make the proximal, middle or distal sections but the rotational link has been heat treated to weaken the strength of the rotational link or any combination thereof.

The stent 20 has a reduced state and a non-reduced state. In the non-reduced state, the proximal section 22, the middle section 24 and the distal section 26 have the same diameter thereby forming a circular tubular structure. When the stent 20 is in a reduced state on a catheter assembly 50, the middle section 24 has a reduced diameter $d_2$ that is greater than the reduced diameter $d_1$ of the proximal section 22 or the distal section 26. In addition, the reduced diameter $d_2$ of the middle section 24 in conjunction with the rotational links 40a and 40b allow the middle section 24 to rotate axially about the catheter assembly 50 in relation to the proximal section 22 and the distal section 26. Thus, when a catheter assembly 50, with one of the stent 20 embodiments described herein engaged thereon, is advanced through the vasculature, the middle section of the stent 20 can rotate according to the pathway of the vessel. The difference in reduced diameters between the sections 22,24,26 of the stent 20 is shown in FIG. 2.

FIG. 2 shows the stent 20 in FIG. 1 in a reduced state. The middle section 24 has a diameter $d_2$ in the reduced state while the proximal section 22 and the distal section 26 have a diameter $d_1$ in the reduced state. Although in this embodiment, the proximal section 22 and the distal section 26 have the same reduced diameter $d_1$, it is within the scope of the invention for the proximal section reduced diameter ($Pd_1$) and the distal section reduced diameter ($Dd_1$) to be different from each other and smaller than the reduced diameter $d_2$ of the middle section 24. Thus $Pd_1$ could be greater than $Dd_1$, or $Pd_1$ could be smaller than $Dd_1$, while both $Pd_1$ and $Dd_1$ are less than $d_2$.

The reduced diameter of a section of the stent 20 is affected by the number of struts 32 per unit of circumferential ring 30 length, which is the frequency of the struts 32. The number of struts 32 per unit circumferential ring 30 length is affected by the circumferential distance between adjacent struts 32. In FIG. 1 the proximal section 22 and the distal section 26 each have four struts 32 and three turns 34, while the middle section 24 has eight struts 32 and seven turns 34. All the circumferential rings 30 of a particular section of the stent 20 have the same number of struts 32 per unit of circumferential ring 30 length. In at least one embodiment, the circumferential rings of the proximal section have a different number of struts per unit of circumferential ring length than the distal section while both the proximal section and the distal section have fewer struts per unit of circumferential ring length than the middle section. The greater the number of struts 32 per unit of circumferential ring length, the greater the reduced diameter, as illustrated by the middle section 24 of the stent 20 in FIG. 2. The fewer the number of struts 32 per unit of circumferential ring length, the smaller the reduced diameter as illustrated by the proximal section 22 of the stent 20 in FIG. 2.

Figure 10A:
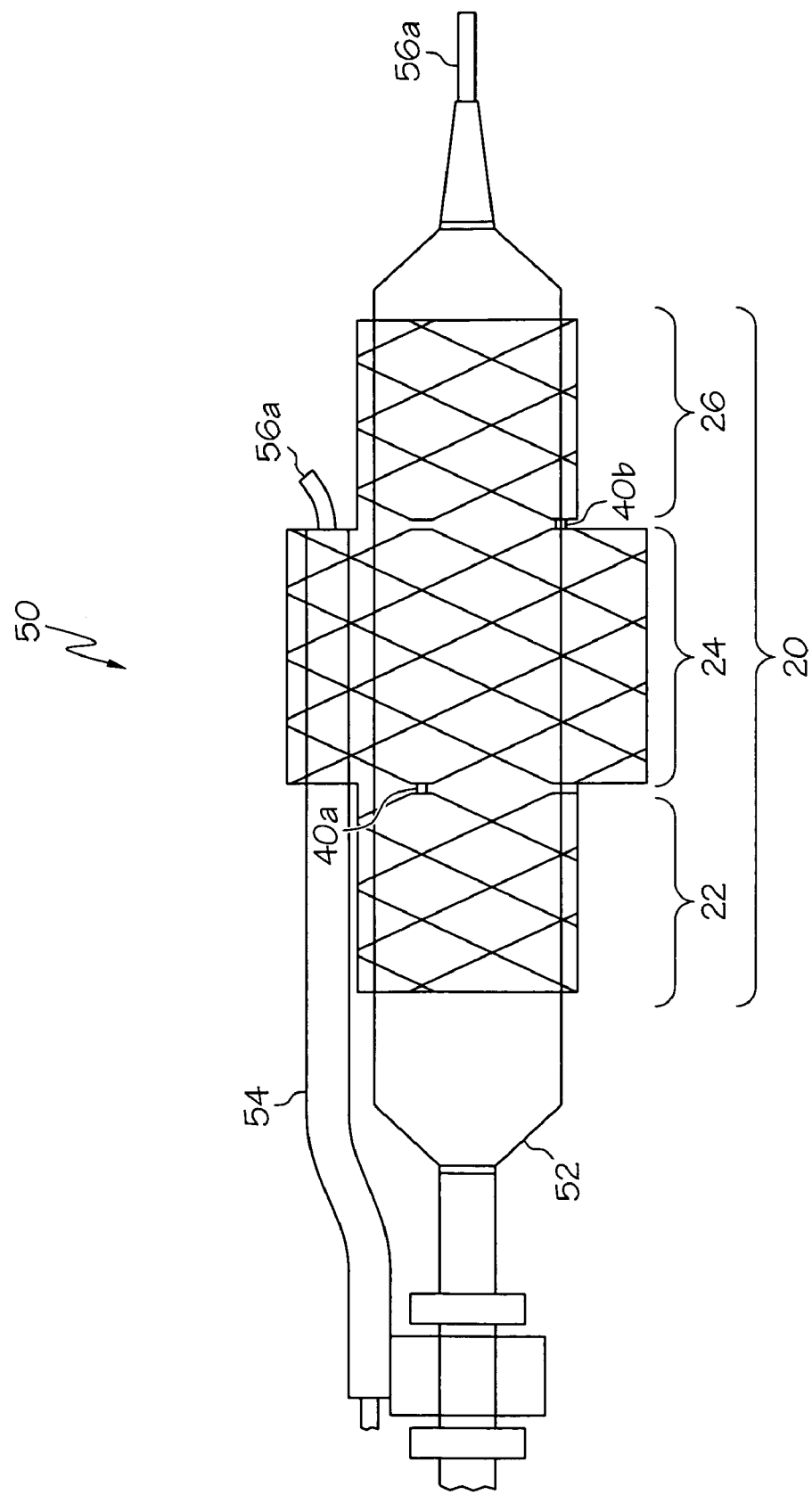
FIG. 10a is a view of an embodiment of the stent on a catheter.

All the embodiments of the stent 20 described herein may be used at a bifurcation. FIG. 10a shows a catheter assembly 50 with one of the embodiments of the inventive stent 20 crimped onto a catheter 52. For simplicity, the pattern of the stent 20 is merely shown as a diamond pattern with spaces between the middle section 24 and the proximal section 22 and the distal section 26 and straight struts 40a and 40b which represent the rotational links 40a and 40b connecting the sections to one another. The stent 20 may have any pattern that incorporates the features of the stent 20 embodiments described herein. The catheter 52 is guided through the vasculature by a guide wire 56a. The catheter assembly 50 has a secondary guide wire 56b housed within a secondary guide wire housing 54. The secondary guide wire housing 54 extends between the catheter 52 and the middle section 24 of the stent 20. The secondary guide wire housing 54 emerges from underneath the middle section 24 of the stent 20 between the middle section 24 and the distal section 26.

Rotational link 40, provides the middle section 24 with the ability to be rotated relative to the end sections 22 and 26. Such rotation or rotational flexibility allows the middle section 24 to be torqued about the axis of a delivery system 50 during advancement without imparting rotation or otherwise significantly affecting the relative position of the end sections 22 and 26. In at least one embodiment, an example of which is illustrated in FIG. 10a, the stent 20 prior to delivery is mounted on a delivery system 50 for use at a vessel bifurcation 60. In the embodiment shown, the secondary or side-branch guide wire housing 54 extends partially under the stent 20 and through a side branch opening 58 in the middle section 24. As the system 50 is advanced to the vessel bifurcation 60 the housing 54 and/or side branch guide wire 56b will tend to impart torque to the system 50 in order to align the side branch opening 58 with the ostium 66 of the side branch vessel 64. The presence of rotational links 40 however, may act to limit the affect of any rotational torque imparted by advancement of the system 50 along the side branch guide wire 56a to substantially the middle section 24 of the stent 20 only, rather than the entire stent 20 and/or delivery system 50. Thus, the rotational links 40 elongate, flex, or shorten as needed to facilitate rotation of the middle section 24. In some embodiments, portions of each rotational link 40 may elongate, flex, or shorten while other portions do not. In some embodiments, portions of the rotational link 40 shorten while other portions elongate or flex.

Figure 10B:
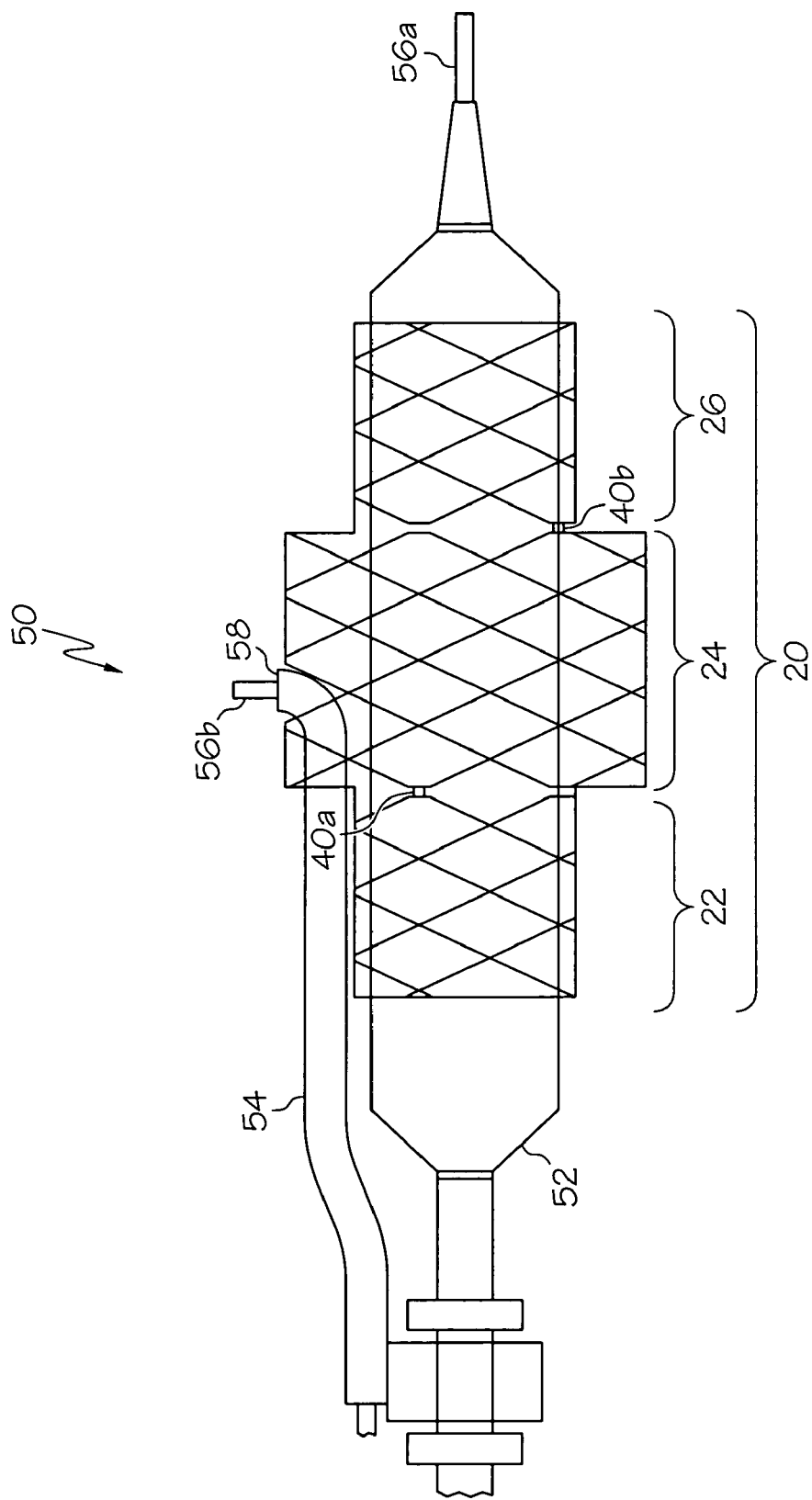
FIG. 10b is a view of another embodiment of the stent on a catheter.
Figure 10C:
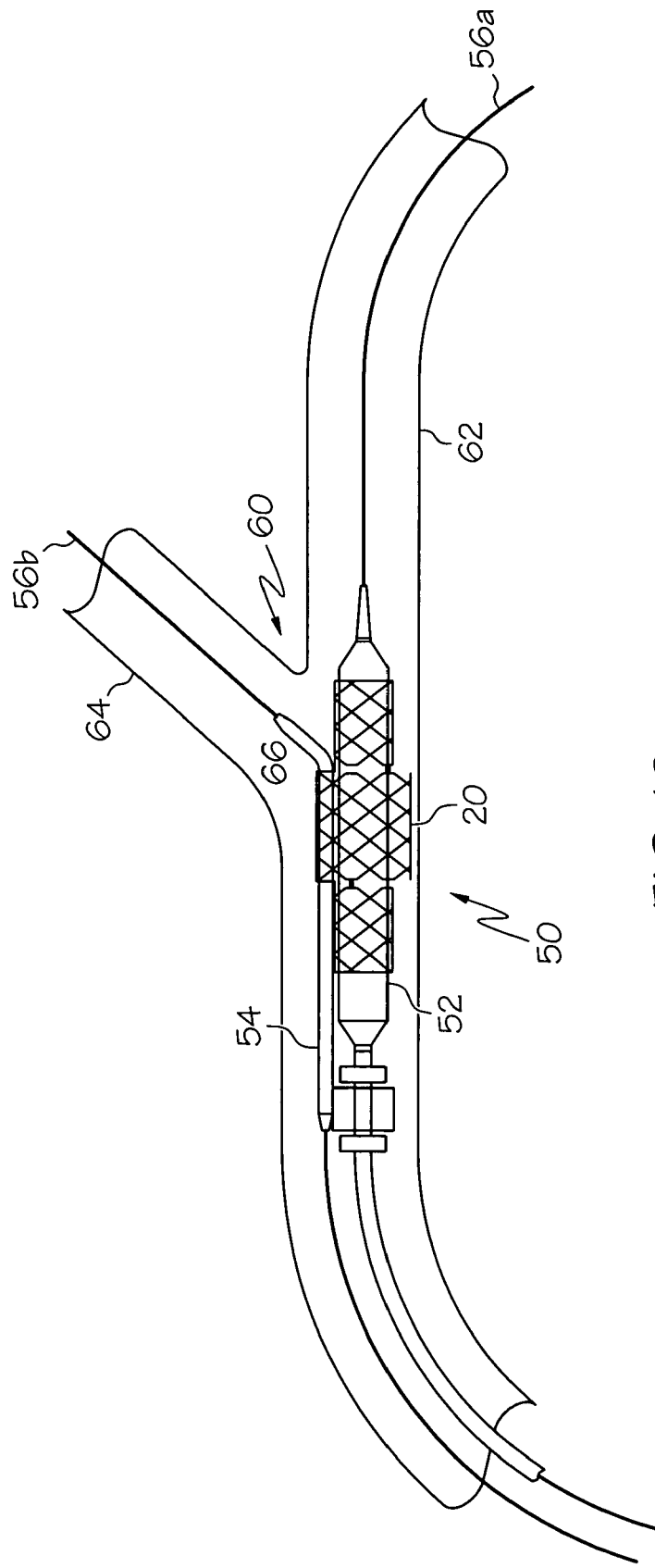
FIG. 10c is a view of the embodiment in FIG. 10a within a vessel at the point of a bifurcation.

FIG. 10c shows the embodiment of FIG. 10a within the vasculature. In use, guide wires 56a and 56b are passed through a lumen or other body vessel to a bifurcation 60. Primary guide wire 56a is then advanced into a primary branch 62 of the bifurcation 60 while the secondary guide wire 56b is advanced into the adjacent or secondary branch 64 of the bifurcation 60. As the system 50 is advanced along both guide wires 56a and 56b, and as a result of the divergent paths defined by the guide wires 56a and 56b, the middle section 24 of the stent 20 will be torqued or rotated relative to the proximal section 22 and the distal section 26 of the stent 20 so that the secondary guide wire housing 54 is in the desired position relative to the secondary branch 64 of the bifurcation 60. In at least one embodiment, the catheter assembly 50 is a fixed wire system, and as such the use of the primary guide wire 56a is unnecessary. In at least one embodiment, the catheter 52 is an over-the-wire, MONORAIL®, or other type of catheter 52 which requires a primary guide wire 56a.

Once the catheter assembly 50 is in the desired position, the stent 20 is expanded. The stent 20 may be expanded by a balloon if the stent 20 is not a self-expanding stent 20. FIG. 10d shows the stent 20 in an expanded state at the bifurcation 60 without the catheter assembly 50. The guide wires 56a and 56b are still present.

FIG. 10b shows a catheter assembly 50 with an alternate embodiment of the stent 20 crimped onto a catheter 52. As with FIG. 10a, the pattern of the stent 20 has been simplified. The stent 20 may have any pattern that incorporates the features of the inventive stent 20. In this embodiment, the secondary guide wire housing 54 extends between the catheter 52 and the middle section 24 of the stent 20 and extends through the middle section 24 into the secondary branch 64, similar to that shown in FIG. 10c. The embodiment shown in FIG. 5 would work in this manner because large cells 28 are formed between the circumferential rings 30 of the middle section 24 because they are out of phase with one another. The size of the cell 28 can be altered to accommodate the secondary guide wire housing 54 by adjusting the lengths of the struts 32 forming the circumferential rings 30 of the middle section 24 or by adjusting the placement of the connecting struts 36. It should be noted that when the secondary guide wire housing 54 extends through the cell 28, the struts forming the cell 28 are distorted only a minimal amount. As such, the actual size of the cell 28 through which the guide wire housing 54 extends is substantially similar size to the cells 28 that are circumferentially adjacent.

In one embodiment, the middle section 24 has a special cell or side branch section that includes either a crown and/or tulip portions through which the secondary guide wire housing 54 extends through the middle section 24. Examples of side branch sections that may be used in the middle section 24 may be found in commonly assigned U.S. patent application Ser. No. 11/273,186, the entire content of which is incorporated by reference herein. Other side branch sections may also be incorporated into the inventive stent.

If a balloon is used on the catheter assembly 50 to expand the stent 20, in at least one embodiment, at least a portion of the balloon may include a coating of one or more low friction materials. In at least one embodiment, the balloon is manufactured from on or more low friction materials. Examples of low friction materials include but are not limited to PTFE or HDPE.

The stent embodiments described herein may be made from any suitable biocompatible materials including one or more polymers, one or more metals or combinations of polymer(s) and metal(s). Examples of suitable materials include biodegradable or bioabsorbable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stent embodiments described herein may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The stent embodiments described herein may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising a proximal section, a middle section, a distal section, a first rotational link, and a second rotational link, each section having a reduced diameter, the reduced diameter of the middle section being greater than the reduced diameter of both the distal section and the proximal section, the first rotational link extending substantially about the entire circumference of the stent and engaging the middle section to the proximal section, the first rotational link engaged to each section at only one location, and the second rotational link extending substantially about the entire circumference of the stent and engaging the middle section to the distal section, the second rotational link engaged to each section at only one location.

2. The stent of claim 1, each section comprising at least one circumferential ring, the at least one circumferential ring comprising a plurality of struts, the at least one circumferential ring of the middle section having the greatest number of struts.

3. The stent of claim 2, the at least one circumferential ring of the proximal section having a different number of struts from the at least one circumferential ring of the distal section.

4. The stent of claim 2, the at least one circumferential ring of the middle section out of phase with the adjacent at least one circumferential ring of the middle section.

5. The stent of claim 2, the at least one circumferential ring of the proximal section out of phase with the at least one circumferential ring of the distal section.

6. The stent of claim 1, the proximal section out of phase with the distal section.

7. The stent of claim 1, the two rotational links each having a proximal end and a distal end, the proximal ends engaging the sections at a first circumferential location, the distal ends engaging the sections at a second circumferential location, the first circumferential location different from the second circumferential location.

8. The stent of claim 7, the proximal end of the first rotational link engaged to the proximal section, and the proximal end of the second rotational link engaged to the middle section.

9. The stent of claim 1, each section comprising at least one circumferential ring, the at least one circumferential ring comprising a plurality of struts, the struts of the circumferential ring of the middle section having the greatest axial length.

10. The stent of claim 1, each section comprising at least one circumferential ring, the at least one circumferential ring comprising a plurality of struts, the struts of the at least one circumferential ring of the middle section having the greatest width.

11. The stent of claim 1, the rotational link comprising struts, the rotational struts having a width, each section comprising at least one circumferential ring, the at least one circumferential ring comprising a plurality of struts, the plurality of struts having a width, the width of the rotational struts less than the width of the plurality of struts.

12. The stent of claim 1, the rotational link comprising struts, each section comprising at least one circumferential ring, the at least one circumferential ring comprising a plurality of struts, the rotational link having a higher frequency of struts than the at least one circumferential ring.

13. The stent of claim 1, the rotational link comprising struts, the rotational struts having a thickness, each section comprising at least one circumferential ring, the at least one circumferential ring comprising a plurality of struts, the plurality of struts having a thickness, the thickness of the rotational struts less than the thickness of the plurality of struts.

14. The stent of claim 1, the rotational link manufactured from a first material, the proximal, middle and distal sections manufactured from a second material, the first material having a lower material strength than the second material.

15. The stent of claim 1, the rotational link, the proximal section, the middle section and the distal section manufactured from a first material, the rotational link having a lower material strength through localized annealing.

16. The stent of claim 1 further comprising at least one radiopaque marker.

17. The stent of claim 1 further comprising a therapeutic agent, the therapeutic agent selected from at least one member of the group consisting of a non-genetic therapeutic agent, a genetic therapeutic agent, cellular material, a polymer agent, and any combination thereof.

18. A system, the system comprising a stent, the stent comprising a proximal section, a middle section, a distal section, a first rotational link, and a second rotational link, each section having a reduced diameter, the reduced diameter of the middle section being greater than the reduced diameter of either the distal section and proximal section, the first rotational link extending substantially about the entire circumference of the stent and engaging the middle section to the proximal section, the first rotational link engaged to each section at only one location, and the second rotational link extending substantially about the entire circumference of the stent and engaging the middle section to the distal section, the second rotational link engaged to each section at only one location, the system further comprising a balloon, the reduced diameters of the proximal section and the distal section causing the stent to engage the balloon, and the first and second rotational links allowing the middle section to rotate about the balloon.

19. The system of claim 18, wherein the reduced diameters of the proximal section and the distal section are different.

20. The stent of claim 18, the rotational link comprising struts, the rotational struts having a width, each section comprising at least one circumferential ring, the at least one circumferential ring comprising a plurality of struts, the plurality of struts having a width, the width of the rotational struts less than the width of the plurality of struts.

21. The stent of claim 18, the rotational link comprising struts, each section comprising at least one circumferential ring, the at least one circumferential ring comprising a plurality of struts, the rotational link having a higher frequency of struts than the at least one circumferential ring.

22. The stent of claim 18, the rotational link comprising struts, the rotational struts having a thickness, each section comprising at least one circumferential ring, the at least one circumferential ring comprising a plurality of struts, the plurality of struts having a thickness, the thickness of the rotational struts less than the thickness of the plurality of struts.

23. The stent of claim 18, the rotational link manufactured from a first material, the proximal, middle and distal sections manufactured from a second material, the first material having a lower material strength than the second material.

24. The stent of claim 18, the rotational link, the proximal section, the middle section and the distal section manufactured from a first material, the rotational link having a lower material strength through localized annealing.

* * * * *